(12) United States Patent
Ullrich et al.

(10) Patent No.: US 9,011,851 B2
(45) Date of Patent: Apr. 21, 2015

(54) INHIBITORS OF HER3 ACTIVITY

(75) Inventors: Axel Ullrich, München (DE); Edward Htun-Van Der Horst, München (DE)

(73) Assignee: Max-Planck-Gesellschaft zur Foerderung der Wissenschaften e.V., Munich (DE)

(*) Notice: Subject to any disclaimer, the term of this patent is extended or adjusted under 35 U.S.C. 154(b) by 2228 days.

(21) Appl. No.: 10/486,113

(22) PCT Filed: Aug. 9, 2002

(86) PCT No.: PCT/EP02/08938
§ 371 (c)(1),
(2), (4) Date: Feb. 9, 2004

(87) PCT Pub. No.: WO03/013602
PCT Pub. Date: Feb. 20, 2003

(65) Prior Publication Data
US 2004/0197332 A1 Oct. 7, 2004

(30) Foreign Application Priority Data
Aug. 9, 2001 (EP) .................................. 01119260

(51) Int. Cl.
| *A61K 39/395* | (2006.01) |
| *A61K 49/16* | (2006.01) |
| *C07K 16/32* | (2006.01) |
| *C07K 16/30* | (2006.01) |
| *A61K 47/48* | (2006.01) |
| *A61K 39/00* | (2006.01) |
| *G01N 33/532* | (2006.01) |
| *C07K 16/28* | (2006.01) |

(52) U.S. Cl.
CPC ........... *C07K 16/32* (2013.01); *A61K 47/48384* (2013.01); *A61K 2039/572* (2013.01); *G01N 33/532* (2013.01); *C07K 16/2863* (2013.01); *A61K 39/39558* (2013.01); *C07K 2317/73* (2013.01); *C07K 2317/76* (2013.01)

(58) Field of Classification Search
CPC ........... A61K 39/395; A61K 39/39533; A61K 39/39558; A61K 47/48384; A61K 47/48507; A61K 47/48561; A61K 47/48569; A61K 47/48584; A61K 2039/572; C07K 16/2863; C07K 2317/14; G01N 33/531; G01N 33/532
USPC ...................... 424/130.1, 134.1, 135.1, 143.1; 530/287.1, 388.22, 391.1, 391.3, 530/391.7; 3/130.1, 134.1, 135.1, 143.1
See application file for complete search history.

(56) References Cited

U.S. PATENT DOCUMENTS

| 5,480,968 A | 1/1996 | Kraus et al. |
| 5,804,396 A | 9/1998 | Plowman |
| 5,968,511 A * | 10/1999 | Akita et al. ................ 424/141.1 |
| 6,277,640 B1 | 8/2001 | Bennett et al. |

FOREIGN PATENT DOCUMENTS

| CN | 1214695 A | 4/1999 |
| CN | 1225129 A | 8/1999 |
| EP | 0 444 961 A1 | 9/1991 |
| WO | WO 94/02602 A1 | 2/1994 |
| WO | WO 97 35885 A | 10/1997 |
| WO | WO 97/35885 A1 | 10/1997 |
| WO | WO 00 31048 A | 6/2000 |
| WO | WO 00 78347 A | 12/2000 |
| WO | WO 01/15730 A1 | 3/2001 |
| WO | WO 02/060470 A1 | 8/2002 |
| WO | 03013602 A1 | 2/2003 |
| WO | WO 03/013602 A1 | 2/2003 |

OTHER PUBLICATIONS

Rudikoff, Proc. Natl. Acad. Sci. USA, 79: 1979-1982.*
Sliwkowski, M.X. et al. J. Biol. Chem., 269(20): 14661-14665, 1994.*
Lee, H. et al., Cancer Research, 61: 4467-4473, 2001, Jun.*
Webster's New World Medical Dictionary, http://www.xreferplus.com/entry/2433389.*
Landgraf, R., and Eisenberg, D. Biochemistry, 39: 8505-8511, 2000.*
Chen, X. et al., Journal of Biological Chemistry, 27(13): 7620-7629, 1996.*
Glennie, M.J. et al., Immunology Today, 21(8): 403-410, 2000.*
Barok, M. et al., Mol. Cancer Ther. 6(7): 2065-2072, 2007.*
Funakoshi, S. et al., Journal of Immunotherapy, 19(2): 93-101, 1996.*
Kono, K. et al., Cancer Research 62: 5813-5817, 2002).*
Gilmour, L.M. R., et al., Clinical Cancer Res. 8: 3933-3942, 2002.*
Millipore/Upstate catalog, p. 16, 2007.*
R. Vadlamudi et al., "Regulation of cyclooxygenase-2 pathway by HER2 receptor." *Oncogene*, vol. 18, No. 2, 14 January 199, pp. 305-314.
Brockhoff et al., "Epidermal growth factor receptor, c-erbB2 and c-erbB3 receptor interaction, and related cell cycle kinetics of SK-BR-3 and BT474 breast carcinoma cells," Cytometry, vol. 44, pp. 338-348, 2001.
Burgess, "EGFR family: Structure Physiology signalling and therapeutic targets," Growth Factors, vol. 26, No. 5, pp. 263-274, Oct. 2008.
Deposit receipt for DSM ACC2527, 2 pages, Sep. 11, 2001.
EPO Board of Appeal, Case No. T 0939/92, 30 pages, Decision of Sep. 12, 1995.
EPO Board of Appeal, Case No. T 0210/02, 22 pages, Decision of Oct. 1, 2004.

(Continued)

*Primary Examiner* — Misook Yu
*Assistant Examiner* — Anne Holleran
(74) *Attorney, Agent, or Firm* — Rothwell, Figg, Ernst & Manbeck, P.C.

(57) ABSTRACT

The present invention relates to a pharmaceutical composition comprising as an active agent an inhibitor of HER3 activity, particularly an anti-HER3-antibody. Further, the use of this composition for the diagnosis, prevention or treatment of hyperproliferative diseases, particularly tumor diseases is disclosed.

11 Claims, 43 Drawing Sheets

(56) References Cited

OTHER PUBLICATIONS

EPO Board of Appeal, Case No. T 1329/04, 16 pages, Decision of Jun. 28, 2005.
Fan et al., "Antibody-induced Epidermal Growth Factor Receptor Dimerization Mediates Inhibition of Autocrine Proliferation of A431 Squamous Carcinoma Cells," J. Biol. Chem., vol. 269, No. 44, pp. 27595-27602, Nov. 4, 1994.
Harari et al., "Molecular mechanisms underlying ErbB2/HER2 action in breast cancer," Oncogene, vol. 19, pp. 6102-6114, 2000.
Heitner et al., "Selection of cell binding and internalizing epidermal growth factor receptor antibodies from a phage display library," J. Immunol. Methods, vol. 248, pp. 17-30, 2001.
Hirayama et al., "Complete and Rapid Peptide and Glycopeptide Mapping of Mouse Monoclonal Antibody by LC/MS/MS Using Ion Trap Mass Spectrometry," Anal Chem, vol. 70, No. 13, pp. 2718-2725, Jul. 1, 1998.
Hurwitz et al., "Suppression and promotion of tumor growth by monoclonal antibodies to ErbB-2 differentially correlate with cellular uptake," Proc. Natl. Acad. Sci. USA, vol. 92, pp. 3353-3357, Apr. 1995.
Klapper et al., "Tumor-inhibitory Antibodies to HER-2/ErbB-2 May Act by Recruiting c-Cb1 and Enhancing Ubiquitination of Her-2[1]," Cancer Res., vol. 60, pp. 3384-3388, Jul. 1, 2000.
Lab Vision Corporation Data Sheet, c-erbB-3/HER Oncoprotein Ab-5 (Clone H3.105.5; same as Ab105), 3 pages, 1999.
Lenferink et al., "Differential endocytic routing of homo- and heterodimeric ErbB tyrosine kinases confers signaling superiority to receptor heterodimers," EMBO J., vol. 17, No. 12, pp. 3385-3397, 1998.
Liscovitch et al., "A case study in misidentification of cancer cell lines: MCF-7/AdrR cells (re-designated NCI/ADR-RES) are derived from OVCAR-8 human ovarian carcinoma cells," Cancer Letters, vol. 245, pp. 350-352, 2007.
Millipore Catalogue, 3 pages, 2007.
Millipore Certificate of analysis product information, 3 pages, 2007.
Notice of Opposition to EP Patent No. 1414494, Opponent Sanofi-Aventis, 23 pages, Dec. 3, 2009.
Notice of Opposition to EP Patent No. 1414494, Opponent MedImmune LLC, 12 pages, Dec. 3, 2009.
Notice of Opposition to EP Patent No. 1414494, Opponent F. Hoffmann-La Roche AG and Genentech, Inc., 24 pages, Dec. 3, 2009.
Notice of Opposition to EP Patent No. 1414494, Opponent Merck Patent Gmbh, 26 pages, Dec. 3, 2009.
Notice of Opposition to EP Patent No. 1414494, Opponent Ablynx N.V., 29 pages, Dec. 4, 2009.
Notice of Opposition to EP Patent No. 1414494, Opponent Glaxo Group Limited, 28 pages, Dec. 4, 2009.
Notice of Opposition to EP Patent No. 1414494, Opponent Novartis AG, 14 pages, Dec. 4, 2009.
Notice of Opposition to EP Patent No. 1414494, Opponent Merrimack Pharmaceuticals, Inc., 23 pages, Dec. 4, 2009.
O-Charoenarat et al., "Epidermal Growth Factor-like Ligands Differentially UP-Regulate Matrix Metallooproteinase 9 in Head and Neck Squamous Carcinoma Cells," Cancer Research, vol. 60, pp. 1121-1128, Feb. 15, 2000.
Certificate of Analysis of Upstate Biotechnology, Anti-c-erbB-3/HER-3 (185kDA), Catalog # 05-471, Lot #16638, 6 pages. 2008.
Certificate of Analysis of Millipore, Anti-erbB-3/HER-3 clone H3.105.5, Catalog # 05-471, Lot #DAM1406285, 2 pages, 2007.
Van Der Horst et al., "Anti-HER-3 MAbs inhibit HER-3-mediated signaling in breast cancer cell lines resistant to anti-HER-2 antibodies," Int. J. Cancer, vol. 115, pp. 519-527, 2005.
Wallasch et al., "Heregulin-dependent regulation of HER2/neu oncogenic signaling by heterodimerization with HER3," EBMO J., vol. 14, No. 17, pp. 4267-4275, 1995.
Waterman et al., "Alternative Intracellular Routing of ErbB Receptors May Determine Signaling Potency," J. Biol. Chem., vol. 273, No. 22, pp. 13819-13827, May 29, 1998.

Xu et al., "The Outcome of Heregulin-induced Activation of Ovarian Cancer Cells Depends on the Relative Levels of HER-2 and HER-3 Expression," Clinical Cancer Research, vol. 5, pp. 3653-3660, Nov. 1999.
Zhang et al., "Intravenous RNA Interference Gene Therapy Targeting the Human Epidermal Growth Factor Receptor Prolongs Survival in Intracranial Brain Cancer," Clincal Cancer Research, vol. 10, pp. 3667-3677, Jun. 1, 2004.
Deposit receipt for DSM ACC2527.
Millipore, Anti-rbB-3/HER-3, clone H3.105.5, 4 pages.
NeoMarkers c-erbB-3/HER-3 Oncoprotein Ab-5, Antibody List, 2001, 1 page.
NeoMarkers, c-erbB-3/HER-3 Ab-5 Clone H3.105.5; same as Ab 105, Data Sheet, 1 page.
Upstate Biotechnology, "Anti-c-erb B-3/HER-3 (185kDa)", Catalog #05-471, 1 page.
Upstate cell signalling solutions, Certificate of Analysis, Anti-erbB-3/HER-3, clone H3.105.5, Catalog #05-471, 2 pages.
Artym et al., "ECM Degradation Assays for Analyzing Local Cell Invasion", Methods in Molecular Biology 522(3): 211-219, 2009.
Declaration in the name of Dr. Lin Nie, Dr. Nie's curriculum vitae—10 pgs., 2011.
Hamilton et al., "Effects of Colony Stimulating Factor-1 on human Extravillous Trophoblast Growth and Invasion", Journal of Endocrinology,1998 (159) 69-77.
Soloviev et al.,"Cell Adhesion and Migration Assays", Methods Mol. Med. 129:267-78, 2006.
Vaccine Excipient & Media summary published in Appendix B of the Pink Book: Epidemiology and Prevention of Vaccine-Preventable Diseases by the Centers for Disease Control and Prevention (CDC)—19 pgs., May 2011.
Wu et al., "Inhibition of Head and Neck Squamous Cell Carcinoma Growth and Invasion by the Calcium Influx Inhibitor Carboxyamido-Triazole" Clinical Cancer Research, 1997, (3), 1915-1921.
Prewett et al., "The Biologic Effects of C225, A Chimeric Monoclonal Antibody to the EGFR, on Human Prostate Carcinoma," J. Immunotherapy, vol. 19, No. 6, pp. 419-427, 1997.
Rajkumar et al., "A monoclonal antibody to the human c-erbB3 protein stimulates the anchorage-independent growth of breast cancer cell lines," Br. J. Cancer, vol. 70, pp. 459-465, 1994.
Ricci et al., "Expression of HER/erbB Family of Receptor Tyrosine Kinases and Induction of Differentiation by Glial Growth Factor 2 in Human Rhabdomyosarcoma Cells," Int. J. Cancer, vol. 87, pp. 29-36, 2000.
Rubin et al., "Symposium article: The basic biology of HER2," Annals of Oncology, vol. 12, Suppl. 1, pp. S3-S8, 2001.
Siegel et al., "Elevated expression of activated forms of Neu/ErbB2 and ErbB-3 are involved in the induction of mammary tumors in transgenic mice: implications for human breast cancer," EMBO Journal, vol. 18, No. 8, pp. 2149-2164, 1999.
Smith et al., "Complete Amino Acid Sequence of the Heavy-Chain Variable Region from an A/J Mouse Antigen-Nonbinding Monoclonal Antibody Bearing the Predominant Arsonate Idiotype," Biochemistry, vol. 23, pp. 4726-4732, 1984.
Sridhar, "Chemomodulation of Doxorubicin Pharmacodynamics," Annual Report, Award No. DAMD17-98-1-8109, 40pages, Oct. 2002.
Stemmer et al., "Single-step assembly of a gene and entire plasmid from large numbers of oligodeoxyribonucleotides," Gene, vol. 164, pp. 49-53, 1995.
Sunada et al., "Monoclonal antibody against epidermal growth factor receptor is internalized without stimulating receptor phosphorylation," Proc. Natl. Acad. Sci. USA, vol. 83, pp. 3825-3829, Jun. 1986.
Upstate Biotechnology, 1999 Catalog Products for Cell Signaling Research, 3 pages, 1999.
Upstate Biotechnology, 2000 Catalog Products for Cell Signaling Research, 4 pages, 2000.
Upstate Biotechnology, 2001 Catalog Cell Signaling Research Reagents, 5 pages, 2001.
R. Vadlamudi et al., "Regulation of cyclooxygenase-2 pathway by HER2 receptor." Oncogene, vol. 18, No. 2, 14, pp. 305-314. , 1999.
D. Baeckström et al., "Morphogenetic and proliferative responses to heregulin of mammary epithelial cell in vitro are dependent on HER2

(56) References Cited

OTHER PUBLICATIONS and HER3 and differ from the response . . . " *International Journal of Oncology*, vol. 16, No. 6, Jun. 2000, pp. 1081-1090.

D. Todd et al., "Ionizing radiation stimulates existing signal transduction pathways involving the activation of epidermal growth factor receptor ans erbB-3 . . . ", *Journal of Receptor and Signal Transduction Research*, vol. 19, No. 6, Nov. 1999, pp. 885-908.

T. Rajkumar et al., "A monoclonal antibody to the human c-erbB3 protein stimulates the anchorage-independent growth of breast cancer cell lines", *British Journal of Cancer*, vol. 70, 1994, pp. 459-465.

Adamczyk et al., "Sequencing of anti-thyroxine monoclonal antibody Fab fragment by ion trap mass spectrometry", Rapid Communications in Mass Spectrometry, 14, 2000, pp. 999-1007.

Arteaga et al. "Epidermal Growth Factor Receptors in Human Breast Carcinoma Cells: A Potential Selective target for Transforming Growth Factor", Cancer Research, 54, 1994, pp. 4703-4709.

Badache et al.: Neurofibrosarcoma-derived Schwann cells overexpress platelet-derived growth factor (PDGF) receptors and are Induced to proliferate by PDGF BB, Journal of Cellular Physiology, vol. 177, 1998, pp. 334-342.

Deposit receipt for DSM ACC2527, 2001.

"Experimental Report on antibody induced HER3 degradation and inhibition of HER3 phosphorylation", 3 pages.

Millipore, Anti-rbB-3/HER-3, clone H3.105.5, 4 pages., 2008.

NeoMarkers, Antibody List, "c-erbB-3/HER-3 Oncoprotein Ab-5", 1999, 1 page.

NeoMarkers c-erbB-3/HER-3 Oncoprotein Ab-5, Antibody List, 2001, 1 page

Pages from Upstate Biotechnology Catalogue 2000, 4 pages.

Pages from Upstate Biotechnology Catalog (1999 version), 3 pages.

\* cited by examiner

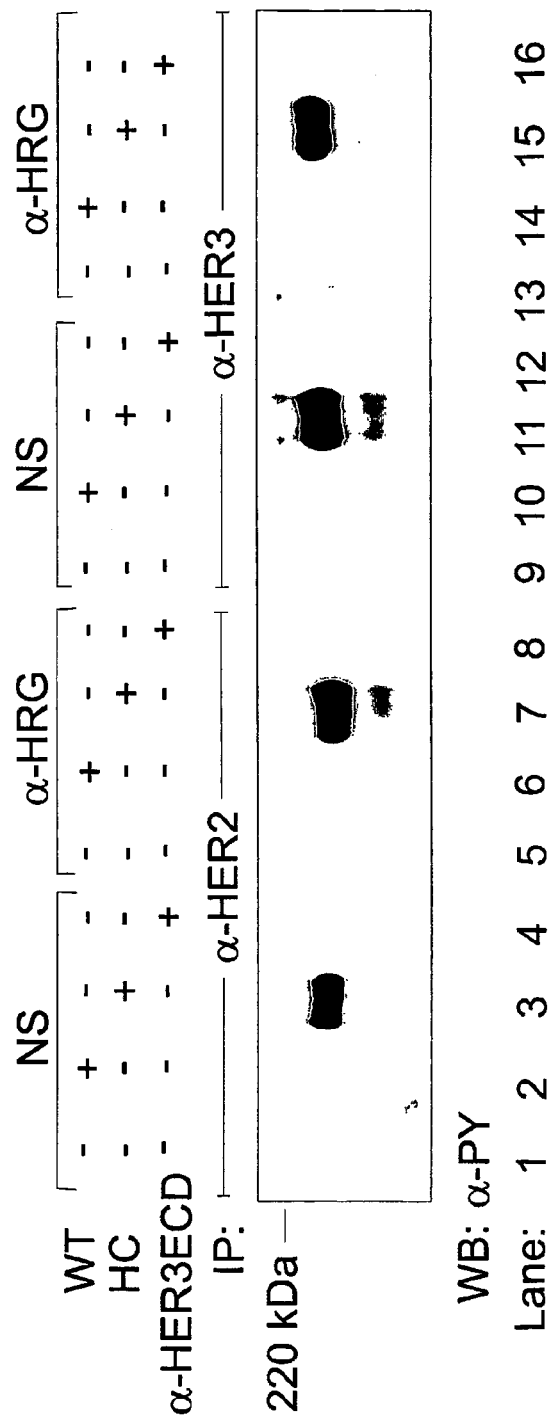

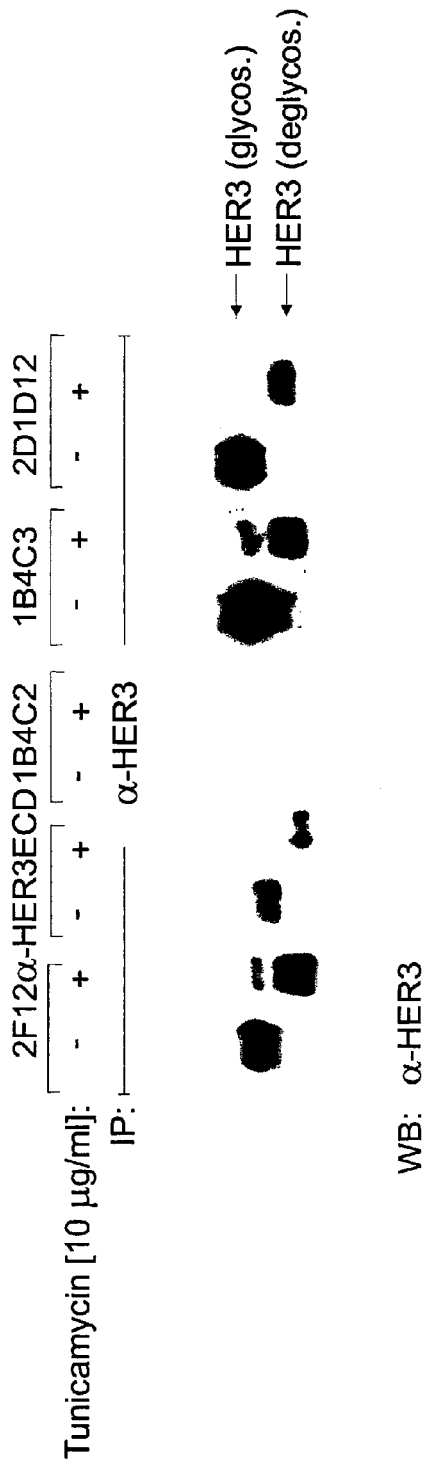
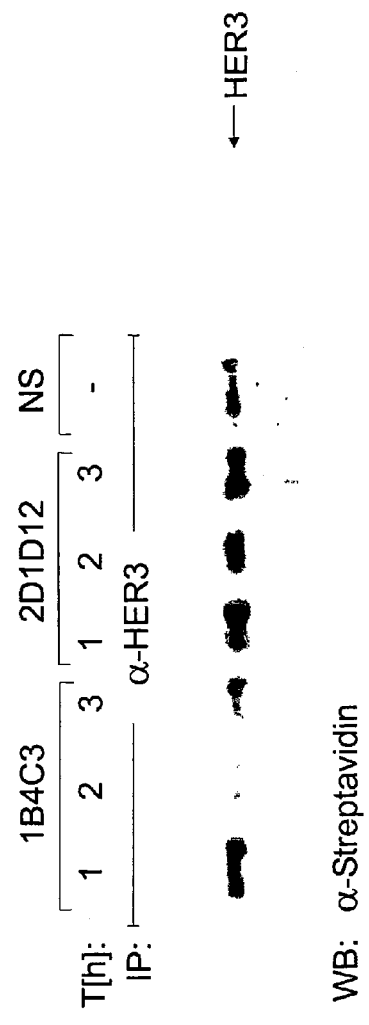
FIG. 6A
FIG. 6B

HER3
MDA-MB-435S

HER3
Mel Juso

Supplementary Data

Supplementary Data

Supplementary Data

Supplementary Data

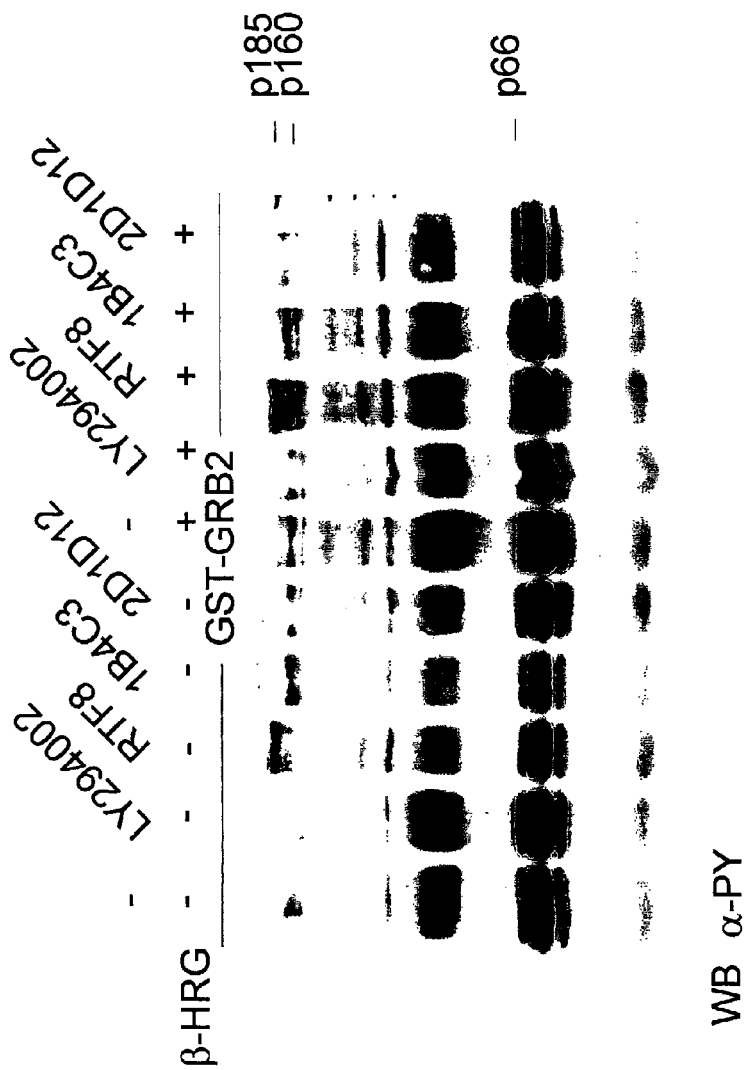
FIG. 9A Supplementary Data

Supplementary Data

Supplementary Data

Supplementary Data ated Aug. 9, 2002, and
INHIBITORS OF HER3 ACTIVITY

CROSS REFERENCE TO RELATED APPLICATION

This application is a 35 USC §371 National Phase Entry Application from PCT/EP02/08938, filed Aug. 9, 2002, and designating the U.S.

BACKGROUND OF THE INVENTION

The present invention relates to a pharmaceutical composition comprising as an active agent an inhibitor of HER3 activity, particularly an anti-HER3-antibody. Further, the use of this composition for the diagnosis, prevention or treatment of hyperproliferative diseases, particularly tumor diseases is disclosed.

Protein tyrosine kinases are known to be enzymes, which mediate signal transduction processes that regulate cell growth and differentiation. Receptor protein tyrosine kinases act via ligand-stimulated tyrosine phosphorylation of substrates. HER3 (also called ErbB3) is a member of the epidermal growth factor receptor (EGFR) subfamily of receptor protein tyrosine kinases (Plowman et al., Proc. Natl. Acad. Sci. U.S.A. 87 (1990), 4905-4909; Kraus et al., Proc. Natl. Acad. Sci. U.S.A. 86 (1989), 9193-9197 and Kraus et al., Proc. Natl. Acad. Sci. U.S.A. 90 (1993), 2900-2904).

HER3 has been found to be overexpressed in several types of cancer such as breast, gastrointestinal and pancreatic cancers. When HER3 is co-expressed with HER2, another member of the EGFR subfamily of receptor protein tyrosine kinases, an active heterodimeric signalling complex is formed.

A monoclonal antibody against HER3 (Rajkumar. et al., Br. J. Cancer 70 (1994), 459-456) had an agonistic effect on the anchorage-independent growth of cell lines expressing HER3. On the other hand, anti-HER3 antibodies described in U.S. Pat. No. 5,968,511 (corresponding to WO 97/35885) are reported to reduce Heregulin-induced formation of HER2/HER3 heterodimers. Such an activity, however, is only demonstrated for an antibody which increases Heregulin binding to HER3. Thus, it is not clear which type of anti-HER3-antibody—if any—has potential of being used for therapeutic applications.

Vadlamudi et al. (Oncogenes 18 (1999), 305-314) describe the regulation of the cyclooxygenase (COX-2) pathway by the HER2 receptor. It was found that a specific inhibitor of COX-2 can suppress the mitogenic and invasive action of colorectal cancer cells. Further, it was found that incubation with a monoclonal anti-HER3 antibody leads to a reduction in the levels HER2/HER3 heterodimers, but results in an only partial reduction of COX-2 expression.

WO 00/31048 discloses a quinazoline derivative which acts as an inhibitor of receptor tyrosine kinases such as EGFR, HER2 and HER4. An inhibition of HER3 is however not disclosed.

WO 00/78347 discloses methods for arresting or inhibiting cell growth, comprising preventing or reducing ErbB-2/ErbB-3 heterodimer formation. For example, the agent may be a combination of an anti-HER2 extracellular domaine antibody and an anti-HER3 antibody, e.g. the HER3 antibody H3.105.5 purchased from Neomarkers. It is however not clear which type of anti-HER3 antibody is required to obtain desirable therapeutic effects.

U.S. Pat. No. 5,804,396 describes a method for identifying an agent for treatment of a proliferative disorder, comprising the steps of assaying a potential agent for activity in inhibition of signal transduction by a HER2/HER3 or HER2/HER4 or HER3/HER4 heterodimer. Specific HER3 inhibitors are not disclosed.

BRIEF SUMMARY OF THE INVENTION

We compared the biological properties of Herceptin, an agonistic monoclonal antibody against HER2 with anti-HER3-antibodies, namely (i) α-HER3-ECD, a murine monoclonal antibody IgG1, Upstate Biotechnology, Cat. No. #05-471, directed against the Heregulin binding site of HER3, (ii) antibody 1B4C3 from our laboratory and (iii) antibody 2D102 also from our laboratory, in invasive breast cancer cell lines MCR-7 (DKFZ Heidelberg), MDA-MB-468 (ATCC HTB-132) and MDA-MB231 (ATCC HTB-26) expressing different HER2:HER3 ratios. We provide evidence that pretreating the breast cancer cell lines with anti-HER3-antibody prior to α/β-Heregulin (α/β-HRG) stimulation diminished the HER2/HER3 tyrosine phosphorylation content in contrast to Herceptin. In addition, anti-HER3-antibody abrogated HER2/HER3 heterodimerization and also reduced the complex formation of the p85 subunit of $PI_3$-kinase and the adaptor protein SHC with HER3, resulting in decreased $PI_3$-kinase and c-jun-terminal kinase activity (JNK), respectively. In comparison to Herceptin, anti-HER3-antibody was also capable of downregulating extracellular signal-regulated kinase 2 (ERK2) after α/β-HRG stimulation. Furthermore, we demonstrate a significant reduction of the migratory and proliferative property of the breast cancer cell lines after pretreatment with anti-HER3-antibody. Our data clearly show that an anti-HER3-antibody is more potent in diminishing signal transduction processes after HRG stimulation than Herceptin. Furthermore, in specific cancer types, e.g. melanoma, anti-HER3 antibodies are effective in reducing migratory and proliferative properties while anti-HER2 antibodies do not show any significant effect at all. These data demonstrate the great potential of anti-HER3 antibodies or other HER3 inhibitors for the therapy of breast cancer and other malignancies characterized by hypersignalling through HER3 and its heterodimerization partners.

Thus, the present invention relates to a pharmaceutical composition comprising as an active agent a specific type of inhibitor of HER3 activity and pharmaceutically acceptable carriers, diluents and/or adjuvants. The HER3 inhibitor of the invention is characterized in that binding of the inhibitor to HER3 reduces HER3 mediated signal transduction. In one embodiment a reduction of HER3 mediated signal transduction may be caused by a downregulation of HER3 resulting in an at least partial disappearance of HER3 molecules from the cell surface. In a further embodiment of the invention the reduction of HER3 mediated signal transduction may be caused by a stabilization of HER3 on the cell surface in a substantially inactive form, i.e. a form which exhibits a lower signal transduction compared to the non-stabilized form.

The inhibitor of the invention may influence the binding of Heregulin to HER3, particularly by decreasing the binding of Heregulin to HER3. In other embodiments, however, the inhibitor may not compete with the binding of Heregulin to HER3.

BRIEF SUMMARY OF THE SEVERAL VIEWS OF THE DRAWINGS

FIG. 6A shows Western blots of MCF7 cells incubated with the monoclonal antibodies 2F12, α-HER3$^{ECD}$, 1B4C2, 1B4C3 and 2D1D12 in the presence or absence of Tunicamycin, precipitated with α-HER3.

FIG. 6B depicts the results of a time course experiment for the effect of 1B4C3 and 2D1D12 on the endocytic processes of HER3 in MCF7 cells incubated for various time periods with 1B4C3 or 2D1D12, respectively, immunoprecipitated with α-HER3, and probed with α-streptavidin.

DETAILED DESCRIPTION OF THE INVENTION

Figure 1A:
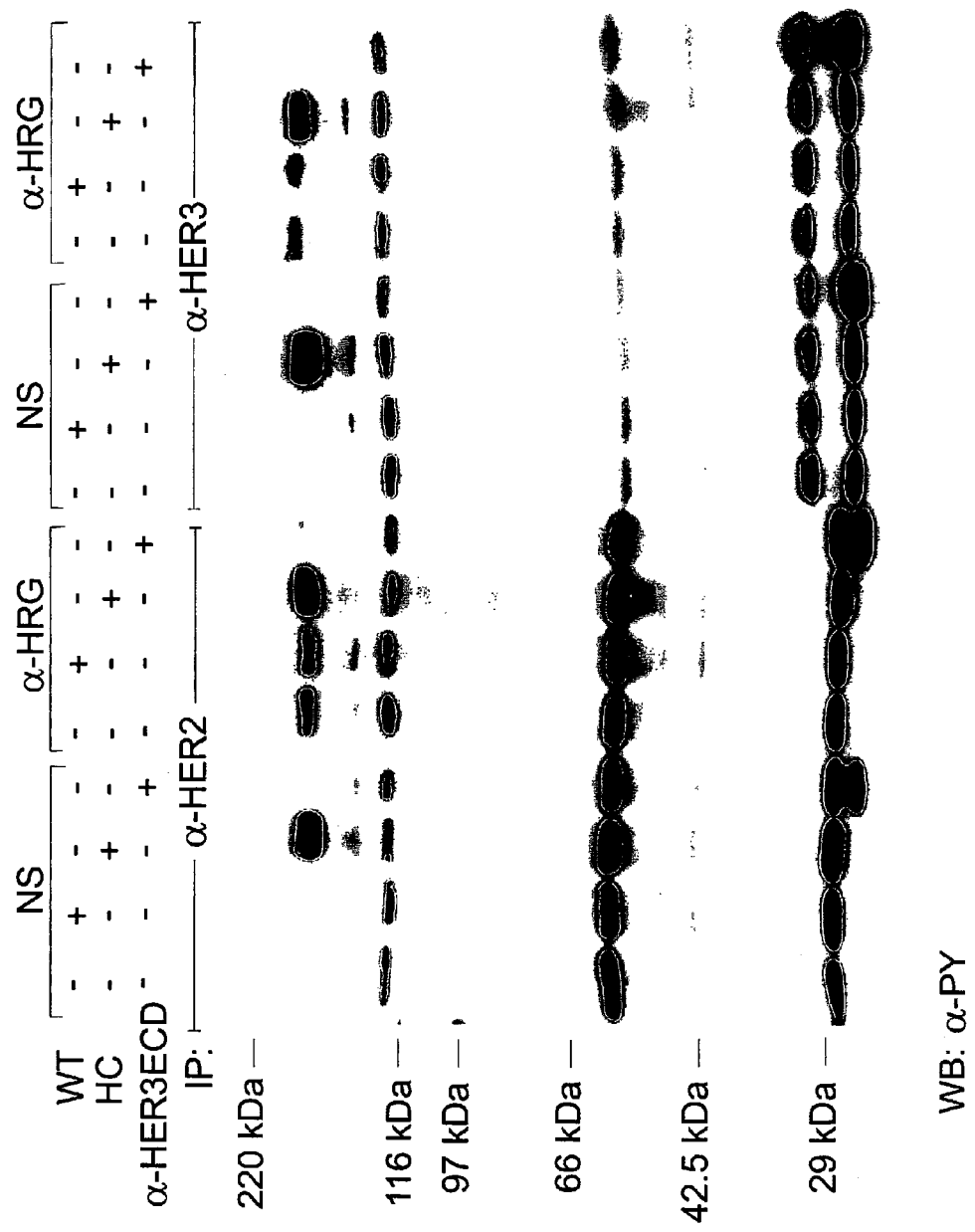
FIG. 1A shows immunoprecipitation of MCF-7$^{ADR}$ cells with α-HER2 and α-HER3. The level of tyrosine phosphorylation was analyzed by Western Blot with anti-PY MAb (upper panels). Reblotting with α-HER2, α-HER3, α-p85, and α-GRB2 antibodies are shown in the middle and bottom panels.
Figure 1A:
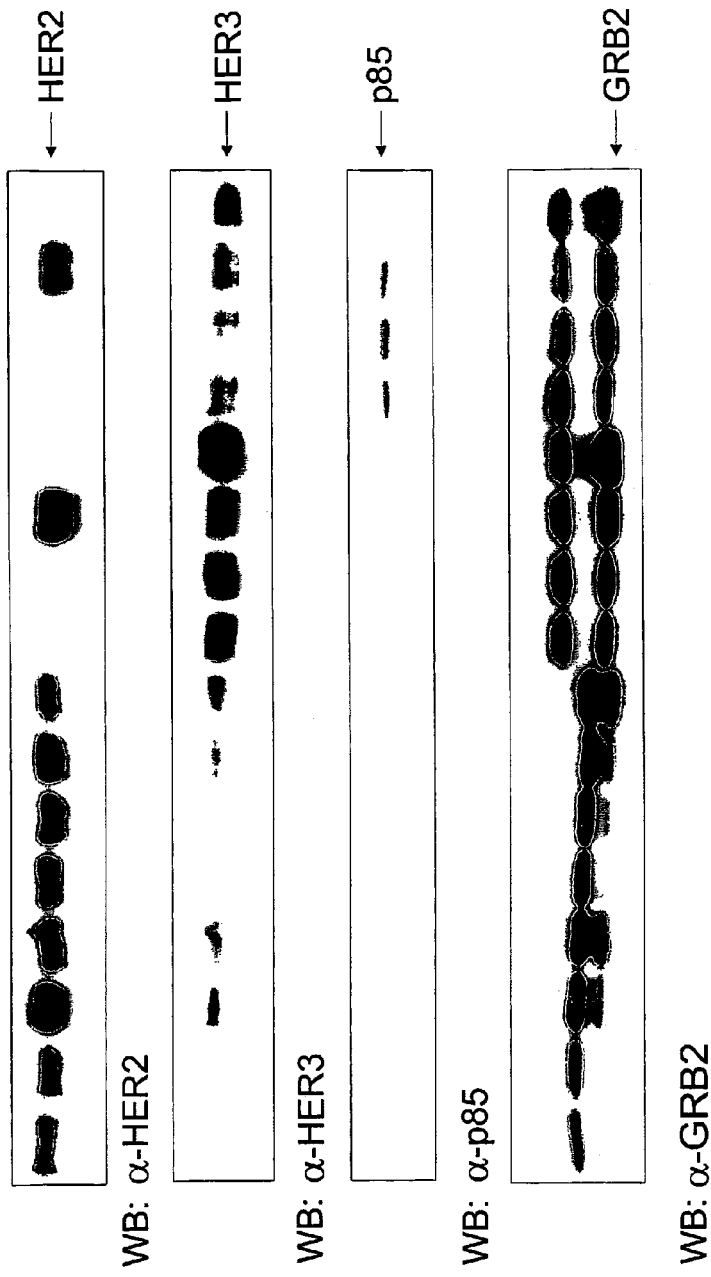

In a preferred embodiment the inhibitor is an anti-HER3-antibody. Preferably, the antibody is directed against the extracellular domain of HER3. It should be noted, however, that also other HER3 inhibitors, particularly low molecular weight inhibitors, e.g. peptides or organic compounds may be used.

According to the invention, the term "antibody" covers monoclonal antibodies, polyclonal antibodies, multispecific antibodies (e.g. bispecific antibodies) formed from at least two antibodies and antibody fragments as long as they exhibit the desired activity.

The antibody may be a monoclonal antibody which may be obtained by the hybridoma method as described by Köhler et al. (Nature 256 (1975), 495) or by recombinant DNA methods (cf. e.g. U.S. Pat. No. 4,816,567). Monoclonal antibodies may also be isolated from phage antibody libraries using techniques described in Clackson et al. (Nature 352 (1991), 624-628) and Marks et al. (J. Mol. Biol. 222 (1991), 581-597). The antibody may be an IgM, IgG, e.g. IgG1, IgG2, IgG3 or IgG4.

Antibody fragments comprise a portion of an antibody, generally the antigen binding or variable region of the intact antibody. Examples of antibody fragments include Fab, Fab', F(ab')$_2$ and Fv fragments, diabodies, single chain antibody molecules and multispecific antibody fragments.

Particularly, the antibody may be a recombinant antibody or antibody fragment, more particularly selected from chimeric antibodies or fragments thereof (Morrison et al., Proc. Natl. Acad. Sci. U.S.A. 81 (1984), 6851-6855), humanized antibodies (Jones et al., Nature 321 (1986), 522-525; Riechmann et al., Nature 332 (1988), 323-329 and Presta, Curr. Op. Struct. Biol. 2 (1992), 593-596), single chain Fv antibodies (Plücktuhn in: The Pharmacology of Monoclonal Antibodies 113, Rosenburg and Moore, EDS, Springer Verlag, N.Y. (1994), pp. 269-315) and diabodies (Hollinger et al., Proc. Natl. Acad. Sci. U.S.A. 90 (1993), 6444-6448).

In an especially preferred embodiment the antibody is selected from antibodies 1B4C3 (IgG2a) and 2D1D12 (IgG1) produced by the hybridoma cell lines DSM ACC 2527 or DSM ACC 2517, fragments thereof or recombinant derivatives thereof. 1B4C3 is an antibody which leads to internalization of HER3 and 2D1D12 is an antibody which leads to stabilization of HER3. Further preferred are antibodies, e.g. chimeric or humanized antibodies or fragments thereof, which have substantially the same biological activity (e.g. as described in the Examples) compared to the antibodies produced by the deposited hybridoma cell lines, for example, by binding to the same epitope on HER3. The hybridoma cell line DSM ACC 2517 was deposited under the Budapest Treaty for the Deposit of Microorganisms on Jul. 24, 2001 at Deutsche Sammlung von Mikroorganismen und Zellkulturen GmbH (DSMZ), Mascheroder Weg 1b, 38124 Braunschweig, Germany. The hybridoma cell line DSM ACC 2527 producing the antibody 1B4C3 was deposited on Aug. 7, 2001 at DSMZ.

The antibody of the invention may be coupled to a labelling group, particularly for diagnostic applications. Examples for suitable labelling groups such as radioactive groups, fluorescent groups or other labelling groups are known in the art. Further, particularly for therapeutic applications, the antibody may be coupled to an effector group, e.g. a cytotoxic group such as a radioactive group, a toxin or another effector group as known in the art.

In a further preferred embodiment, the inhibitor may be selected from non-antibody derived binding proteins such as fibronectin type III domains or anticalins (Skerra, "Engineered protein scaffolds for molecular recognition", J. Mol. Recog. 13 (2000), 167-187 and references cited therein).

Further, the present application relates to the use of an inhibitor of HER3 activity, wherein binding of said inhibitor to HER3 reduces HER3 mediated signal transduction, for the manufacture of an agent for the diagnosis, prevention and/or treatment of hyperproliferative diseases, particularly tumor diseases such as breast cancer, gastrointestinal cancer, pancreas cancer, prostate cancer, glioma, melanoma or other HER3 expressing or overexpressing cancers or formation of tumor metastases. The disease may be associated with increased HER3 signal transduction and may be associated with concomitant HER2 expression or lack of HER2 expression. Particularly the disease is associated with increased HER3 phosphorylation and/or increased HER2/HER3 heterodimerization and/or increased PI$_3$ kinase activity and/or increased c-jun terminal kinase activity and/or AKT activity and/or increased ERK2 activity and/or PYK2 activity.

Surprisingly it was found that the HER3 inhibitor of the invention, particularly an anti-HER3-antibody, shows a significantly higher efficiency in diminishing signal transduction processes than a HER2 inhibitor such as Herceptin. Particularly, in melanoma cells, the anti-HER3-antibody was effective, while Herceptin did not show a significant effect, even though HER2 was expressed by the melanoma cells.

Preferably, the HER3 inhibitor of the invention exhibits at least one of the following characteristics:
- decreasing the association of Heregulin (p85) with transactivated HER3, preferably substantially completely inhibiting the binding of p85 with HER3,
- inhibiting the binding of GRB2 to HER2, the binding of HER2 to HER3 and/or the association of GRB2 with SHC,
- inhibiting receptor tyrosin phosphorylation,
- inhibiting AKT phosphorylation,
- decreasing tumor invasiveness, particularly in breast cancer and melanoma,
- inhibiting PYK2 tyrosine phosphorylation and
- inhibiting ERK2 phosphorylation.

Further, the invention relates to a method for diagnosing, preventing or treating a hyperproliferative disease, particularly a tumor disease, comprising administering a subject in need thereof, e.g. a human, an effective amount of an inhibitor of HER3 activity, wherein binding of said inhibitor to HER3 reduces HER3 mediated signal transduction.

The HER3 inhibitor, particularly the anti-HER3-antibody may be formulated by mixing the active agent with physiologically acceptable carriers, diluents and/or adjuvants, e.g. in the form of lyophilized formulations, aqueous solutions, dispersions or solid preparations such as tablets, dragees or capsules as described in Remington's Pharmaceutical Sciences.

The formulation may also contain more than one active compound, e.g. inhibitors of other receptor protein tyrosine kinases such as EGFR, HER2, HER4 or vascular endothelial factor (VEGF). Alternatively or additionally, the composition may comprise a cytotoxic agent such as doxorubicin, cisplatin or carboplatin, or a cytokine.

The inhibitor of the invention is also suitable for diagnostic applications, e.g. in order to determine the expression and/or activity of HER3 on target cells. Such a diagnostic application may be carried out according to known procedures.

Depending on the type and severity of the disease to be treated, about 1 µg/kg to 15 mg/kg of antibody may be administered to a human patient, e.g. by one or more separate administrations or by continuous infusion. A typical daily dosage might range from about 1 µg/kg to about 100 mg/kg or more, depending on the factors mentioned above. For repeated administrations over several days or longer, depending on the condition to be treated, the treatment is sustained until a desired suppression of disease symptoms occurs.

Further, the present invention shall be explained by the following figures and examples:

EXAMPLES

1. Monoclonal Antibody α-HER3$^{ECD}$ Decreases Receptor Tyrosine Phosphorylation of HER3 and HER2

Figure 1B:
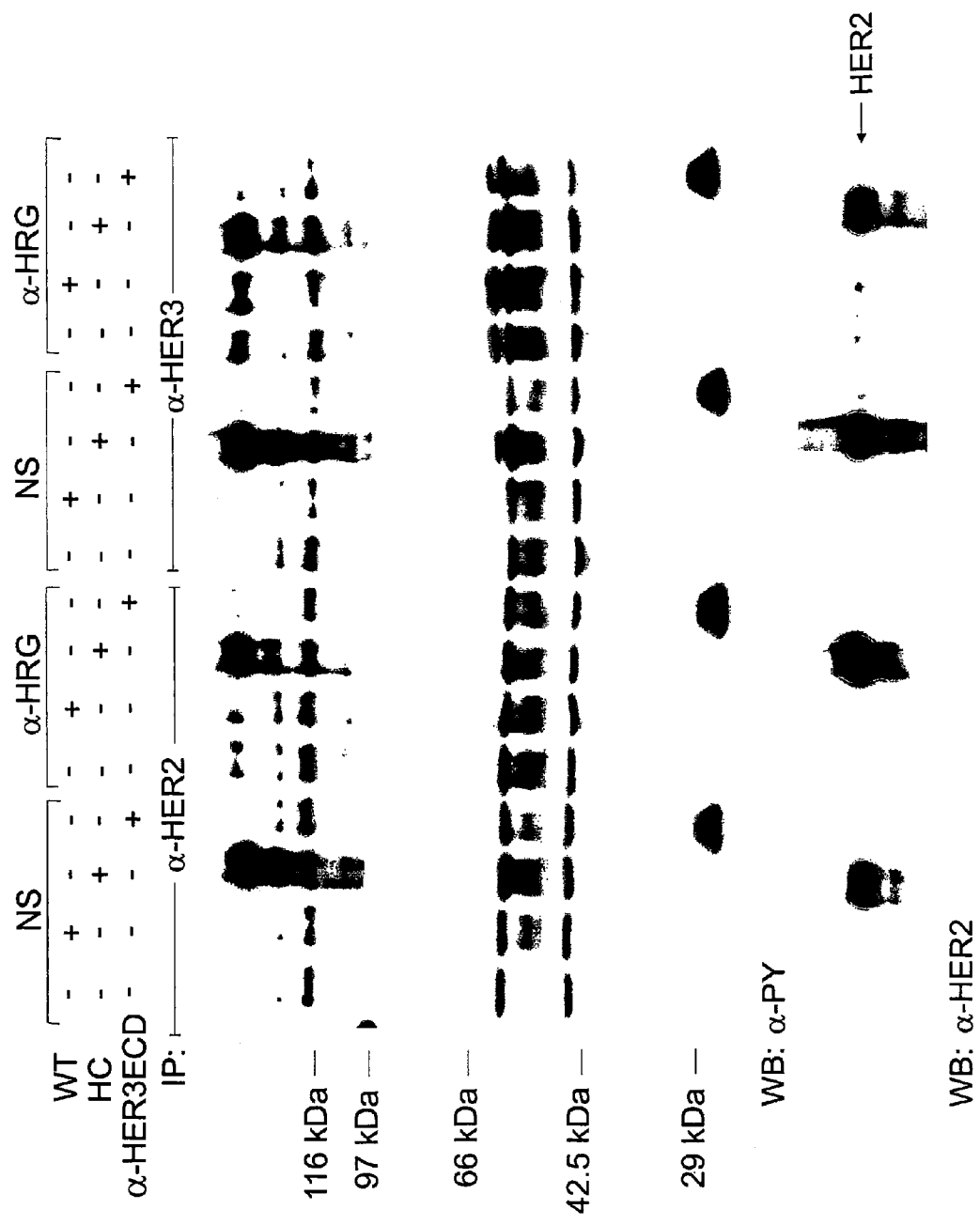
FIG. 1B shows the level of tyrosine phosphorylation in MDA-MB-468 cells as analyzed by Western Blot with anti-PY MAb and α-HER2 (upper panels). The level of tyrosine phosphorylation was analyzed by Western Blot with anti-PY MAb (upper panels). Reblotting with α-HER3, α-p85, α-SHC, and α-GRB2 antibodies are shown in the middle and bottom panels.
Figure 1B:
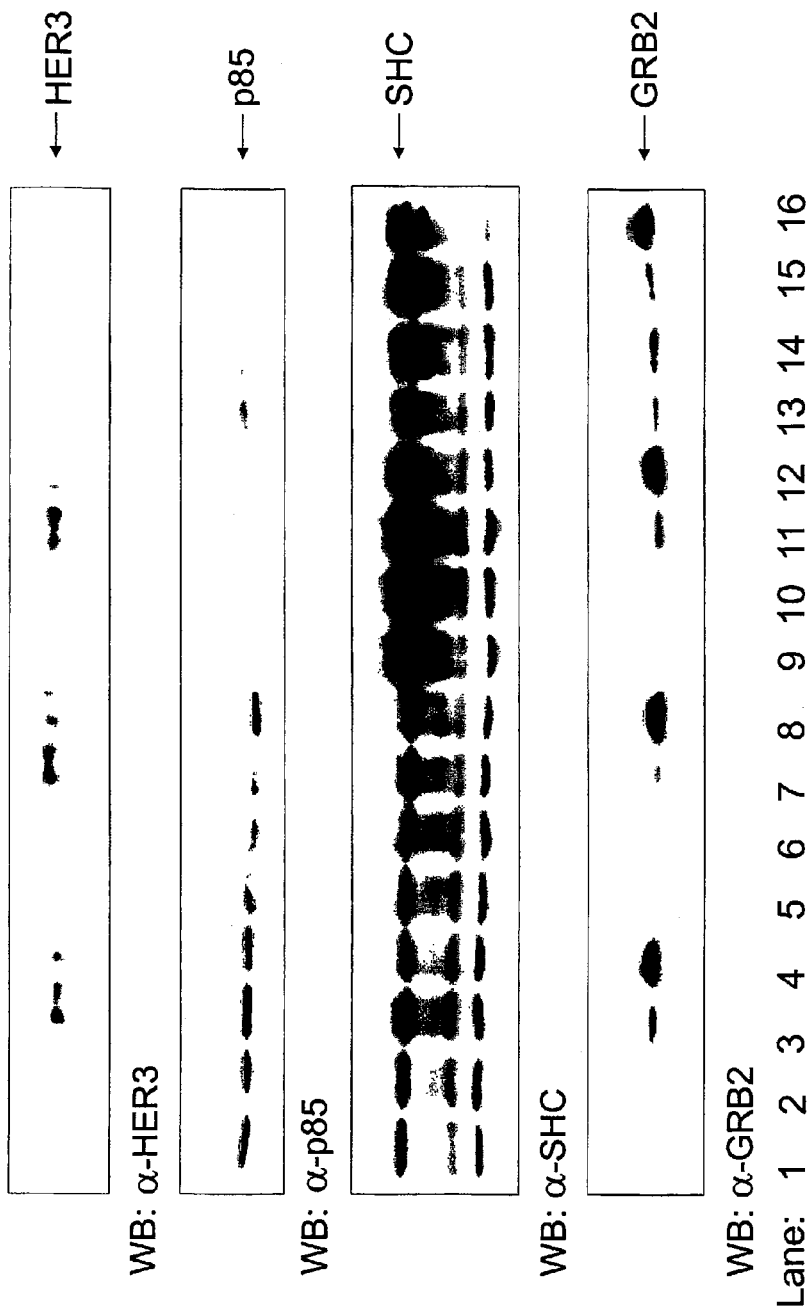
Figure 1C:
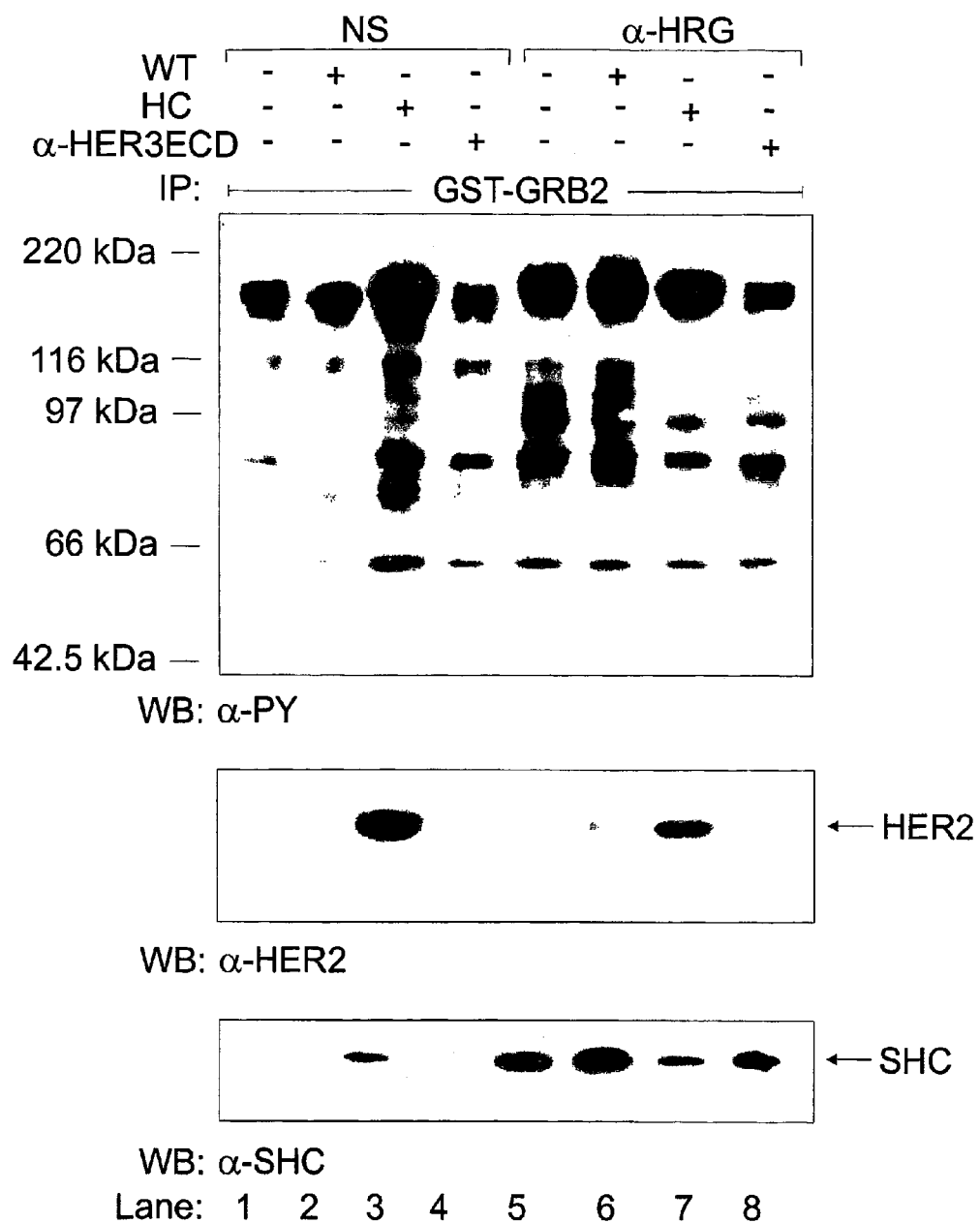
FIG. 1C shows immunoprecipitation of MDA-MB-231 cells with GST-GRB2. The level of tyrosine phosphorylation was analyzed by Western Blot with anti-PY MAb (upper panels). Reblotting with α-HER2 and α-SHC antibodies shows equal protein loading (bottom panels).

The breast cancer cell lines MCF-7 (DKFZ—Heidelberg), MDA-MB-468 (ATCC HTB-132) and MDA-MB-231 (ATCC HTB-26) were chosen on the basis of their different ratios of HER2:HER3 and their inherent migratory properties with MDA-MB-231 being the most invasive cell line. In order to assess the functional role of α-HER3$^{ECD}$ (Upstate Biotechnology, Cat. #05-471) in comparison to trastuzumab (Herceptin), we pretreated the cells with α-HER$^{ECD}$ and HC, respectively, prior to Heregulin (HRG) stimulation, performed receptor-immunoprecipitation experiments and probed with an anti-phosphotyrosine antibody (PY) (FIG. 1). Our data show that pretreatment with α-HER3$^{ECD}$ substantially decreased the tyrosine phosphorylation content of HER3 and HER2 after α-HRG stimulation in MCF-7 (FIG. 1a) and MDA-MB-231 (FIG. 1c), but conversely increased HER3 tyrosine phosphorylation in MDA-MB-468 (FIG. 1b). The association between HER2 and HER3 was even enhanced with α-HER3$^{ECD}$, although the content of tyrosyl-phosphorylated receptors was dramatically reduced (FIG. 1a, b middle upper panel lanes 4 and 8). In contrast, HC upregulated receptor tyrosyl-phosphorylation and promoted association of HER3 and HER2 in the presence or absence of HRG in all cell lines (FIG. 1a, b, c upper panel lanes 3, 7, 11 and 15). In the case of MDA-MB-486 cells, which are insensitive to α-HRG, β-HRG was used as stimulus.

2. α-HER3$^{ECD}$ Abrogates Association of SHC and PI$_3$-K With HER3 and of GRB2 With HER2

Figure 2A:
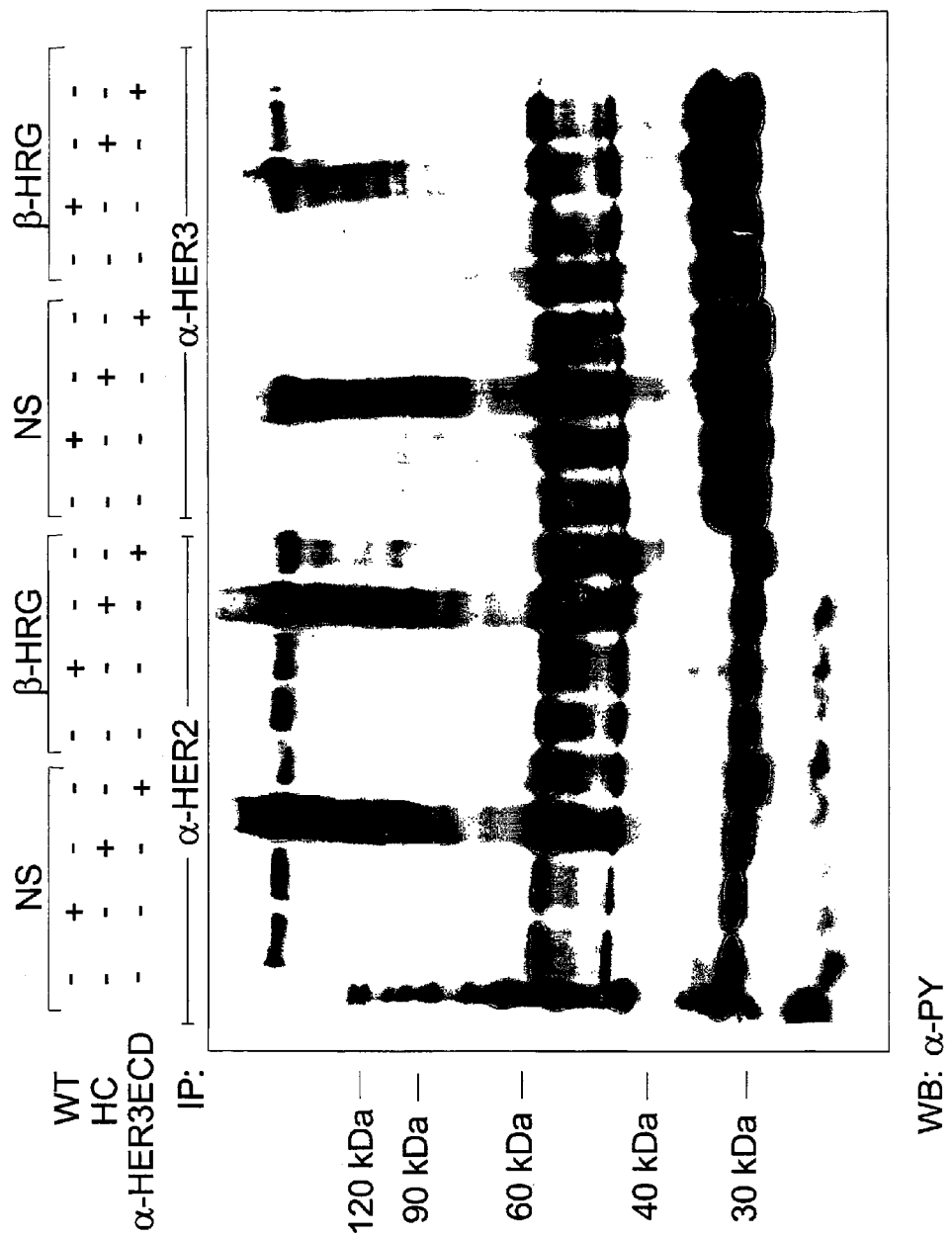
FIG. 2A shows immunoprecipitation of MCF-7$^{ADR}$ cells with α-HER2 and α-HER3. The level of tyrosine phosphorylation was analyzed by Western Blot with anti-PY MAb (upper panels). Reblotting with α-HER2, α-HER3, and α-p85 are shown in the middle panels. Reblotting with α-SHC and α-p85 are shown in the bottom panels.
Figure 2:
FIG. 2B shows immunoprecipitation of MDA-MB-468 cells with α-p85 and α-SHC. The level of tyrosine phosphorylation was analyzed by Western Blot with anti-PY MAb (upper panels). Reblotting with α-HER2 is shown in the upper panels. Reblotting with α-HER3, α-SHC, and α-GRB2 are shown in the bottom panels.
FIG. 2C shows the tyrosyl-phosphorylation of SHC measured by GRB2 binding in GST-pulldown assays in MCF-7$^{ADR}$ cells using GST-GRB2 fusions with α-HER2 and α-HER3 immunoprecipitation.
Figure 2:
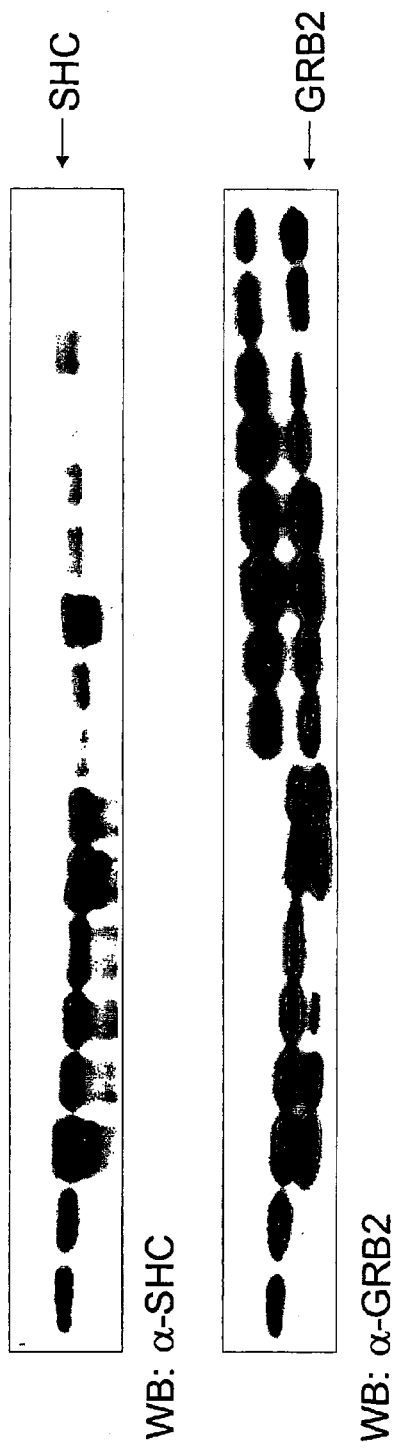
Figure 2B:
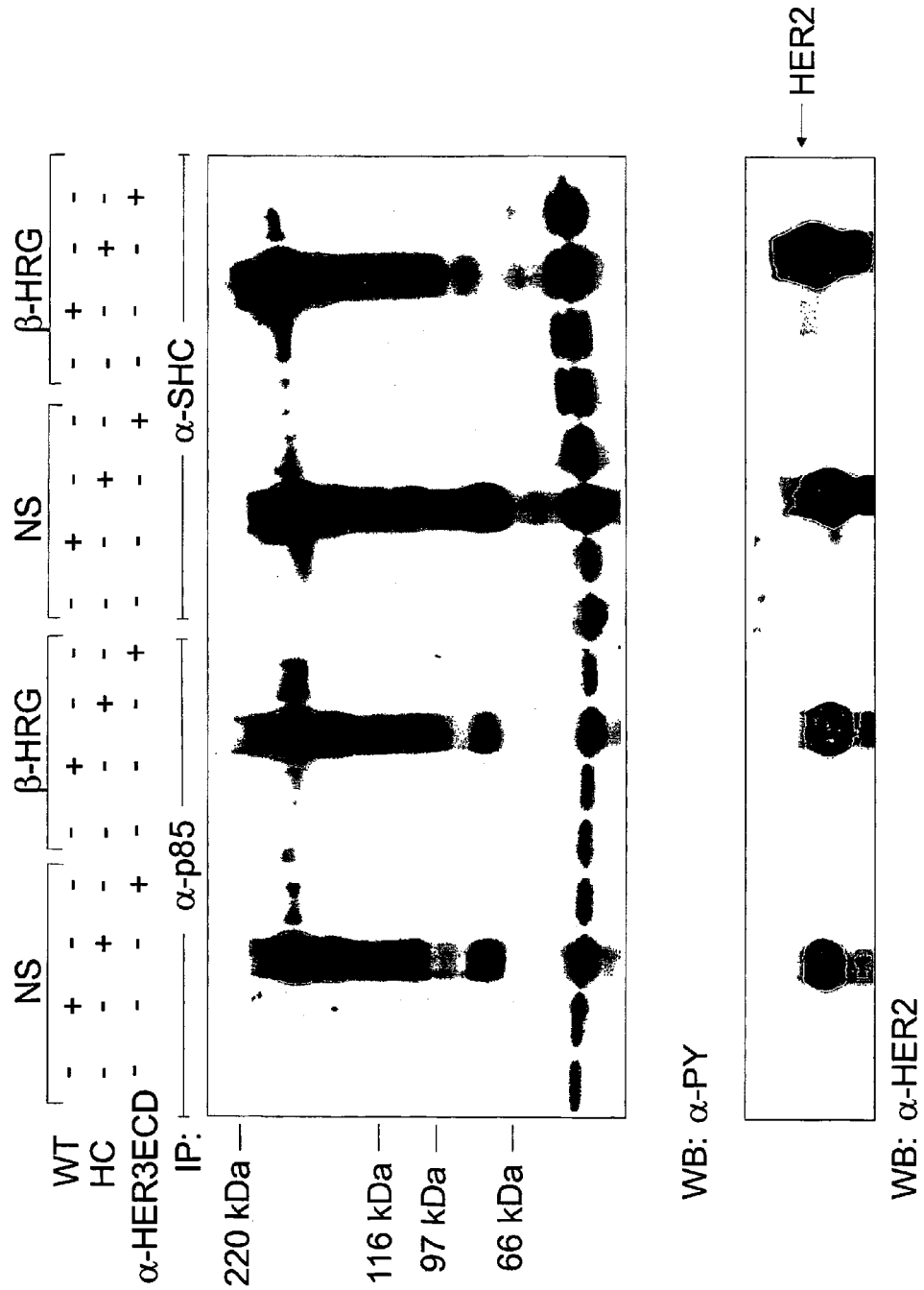
Figure 2:
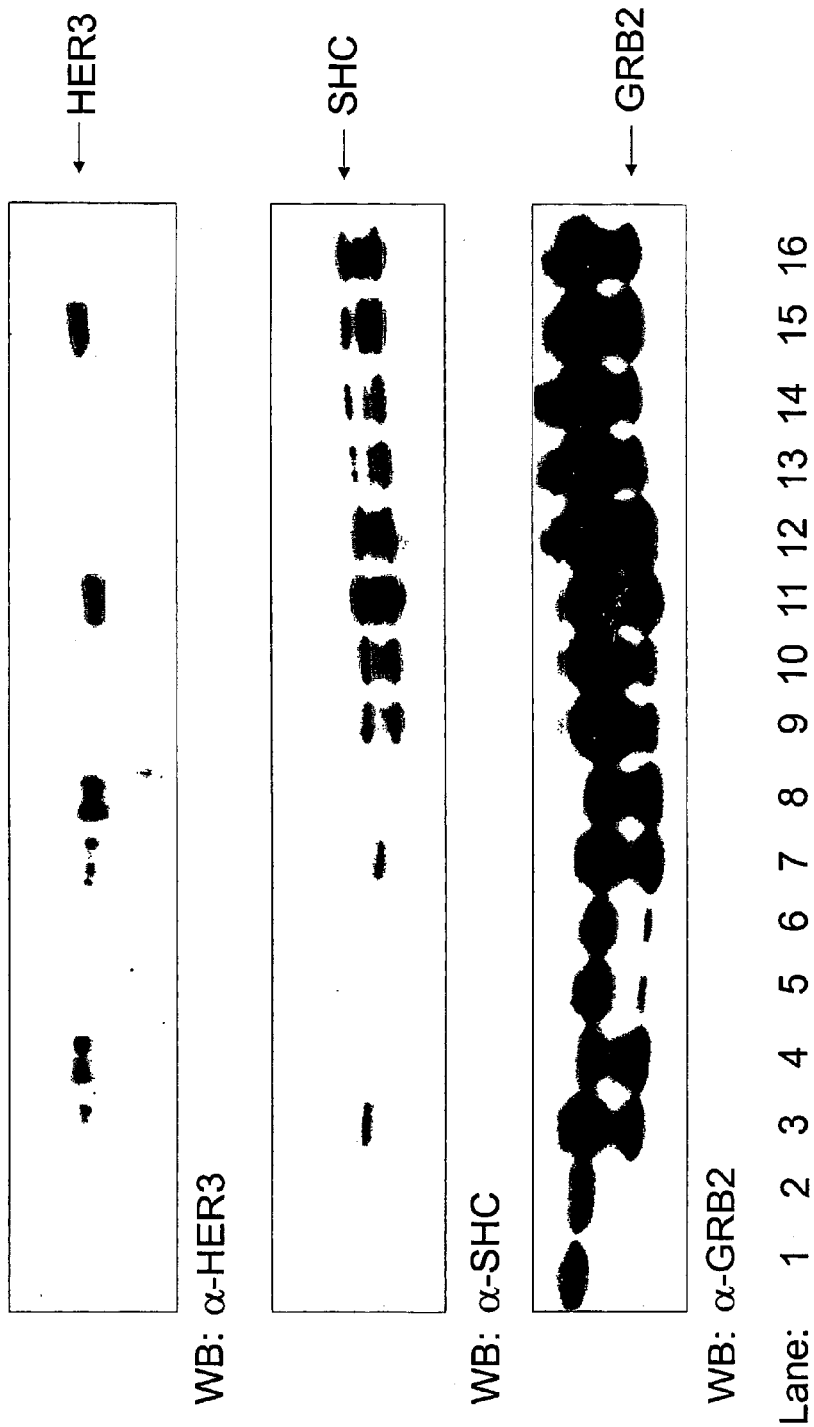

We subsequently asked whether α-HER3$^{ECD}$ has an effect on the known substrates of HER3, namely SHC and phosphatidyl-3-OH-kinase (PI$_3$-K), which are effector proteins responsible for MAPK cascade activation and lipid signalling, respectively. Therefore, we immunoprecipitated SHC and PI$_3$-K under the experimental conditions described above and assessed the tyrosine phosphorylation of these effectors. As shown in FIG. 2, α-HER3$^{ECD}$ significantly decreased the tyrosine phosphorylation of SHC in the cell lines MCF-7 and MDA-MB-486 (FIG. 2a, b compare lane 13 with 16). Interestingly, the association of SHC was attenuated in MCF-7 cells, whereas in MDA-MB-486, α-HER3$^{ECD}$ lead to increased binding of HER3 with SHC. The immunoprecipitates of the regulatory subunit of PI$_3$-K yielded essentially similar results. The binding of tyrosine-phosphorylated HER3 to PI$_3$-K was abrogated in MCF-7, while an increase was observed in MDA-MB-486 (FIG. 1b, 2b). However, pretreatment with α-HER3ECD in MDA-MB-486 cells lead to increased binding of SHC and PI$_3$-K to HER3, whereas HC again showed crosslinking properties in all cell lines. Since SHC associates with the adaptor molecule GRB2 after HRG stimulation, we explored the effect of the reduced tyrosyl-phosphorylation of SHC by measuring GRB2 binding (FIG. 2c). Therefore we performed GST-pulldown assays in MCF-7 cells using GST-GRB2 fusions and the same experimental design as before. Indeed, the reduced tyrosyl-phosphorylation of SHC resulted in strongly decreased binding of GRB2 to SHC (FIG. 2c lower panel, compare lanes 5 and 8), and a complete inhibition of its association with HER2 (FIG. 2c middle panel, compare lanes 5 and 8). These data clearly show that α-HER3$^{ECD}$ inhibits SHC and PI$_3$-K binding to HER3 in MCF-7, but conversely in MDA-MB-486 both proteins associated with HER3 regardless of the phosphorylation status of HER3.

3. α-HER3$^{ECD}$ Downregulates JNK1 and PI$_3$-K Activity

Figure 3A:
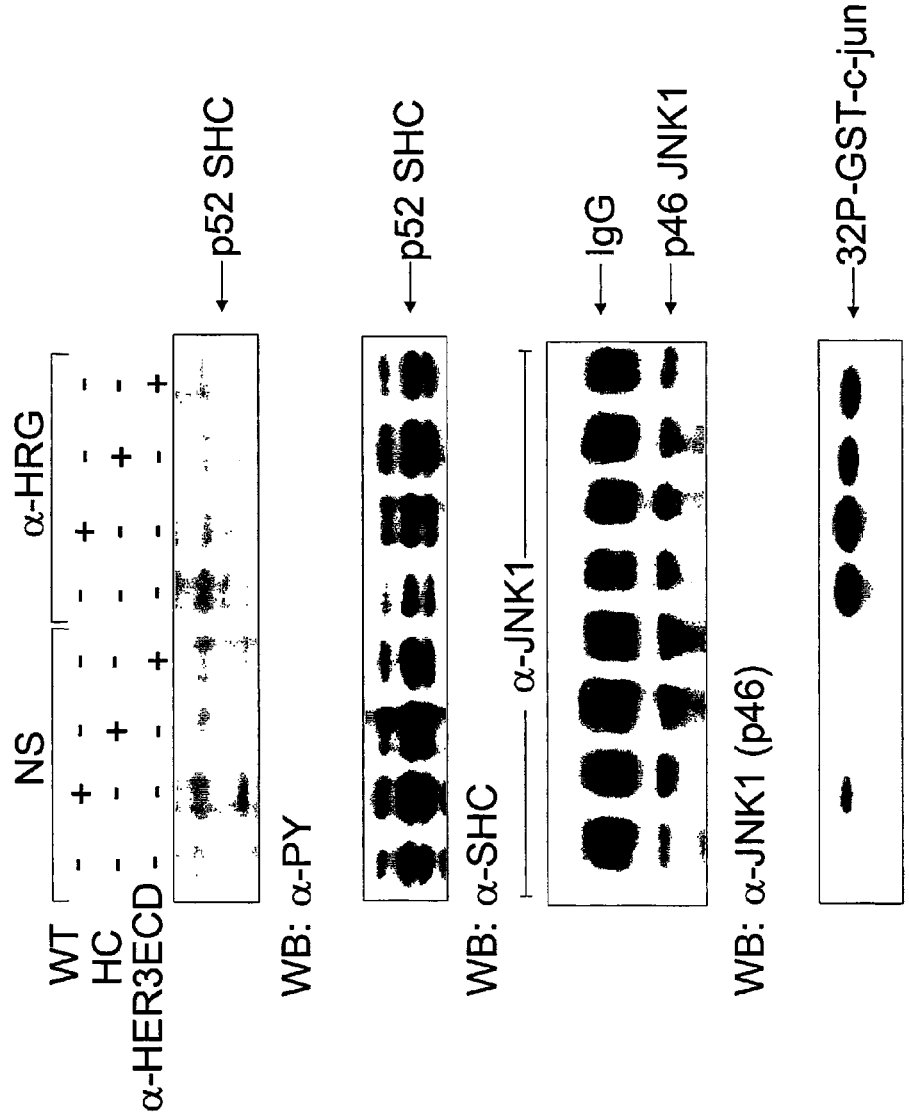
FIG. 3A shows the results of MAPK kinase assays in MCF-7$^{ADR}$ cells. Cell lysates were immunoprecipitated with α-JNK1, additionally probed with a-PY antibody to confirm the effect of α-HER3$^{ECD}$ on SHC tyrosine phosphorylation, and, after stripping, reprobed with α-SHC antibody to determine equal loading of protein (upper and middle panels) An anti-JNK1 antibody (α-JNK1) was used to confirm equal protein loading (middle panel). PI$_3$-K activity is shown in the lower panel.
Figure 3:
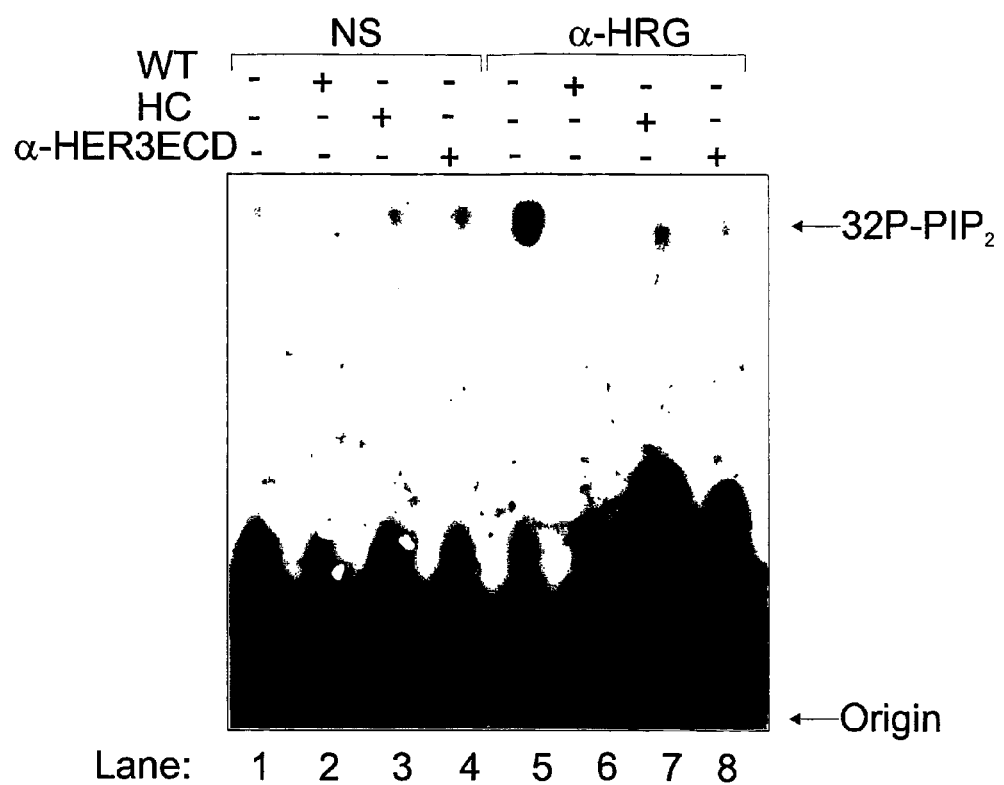
FIG. 3B shows the results of MAPK kinase assays in MDA-MB-468 cells. Cell lysates were immunoprecipitated with α-JNK1, additionally probed with a-PY antibody to confirm the effect of α-HER3$^{ECD}$ on SHC tyrosine phosphorylation, and, after stripping, reprobed with α-SHC antibody to determine equal loading of protein (upper and middle panels) An anti-JNK1 antibody (α-JNK1) was used to confirm equal protein loading (middle panel). PI$_3$-K activity is shown in the lower panel.
FIG. 3C is a JNK kinase assay showing the starved cells pretreated with HC or anti-HER3 and then stimulated for 10 min with HRG, subjected to anti-JNK1 immunoprecipitation and phosphorylation assay using GST-cjun (lower panel). The top panel is a loading control JNK western blot.
Figure 3B:
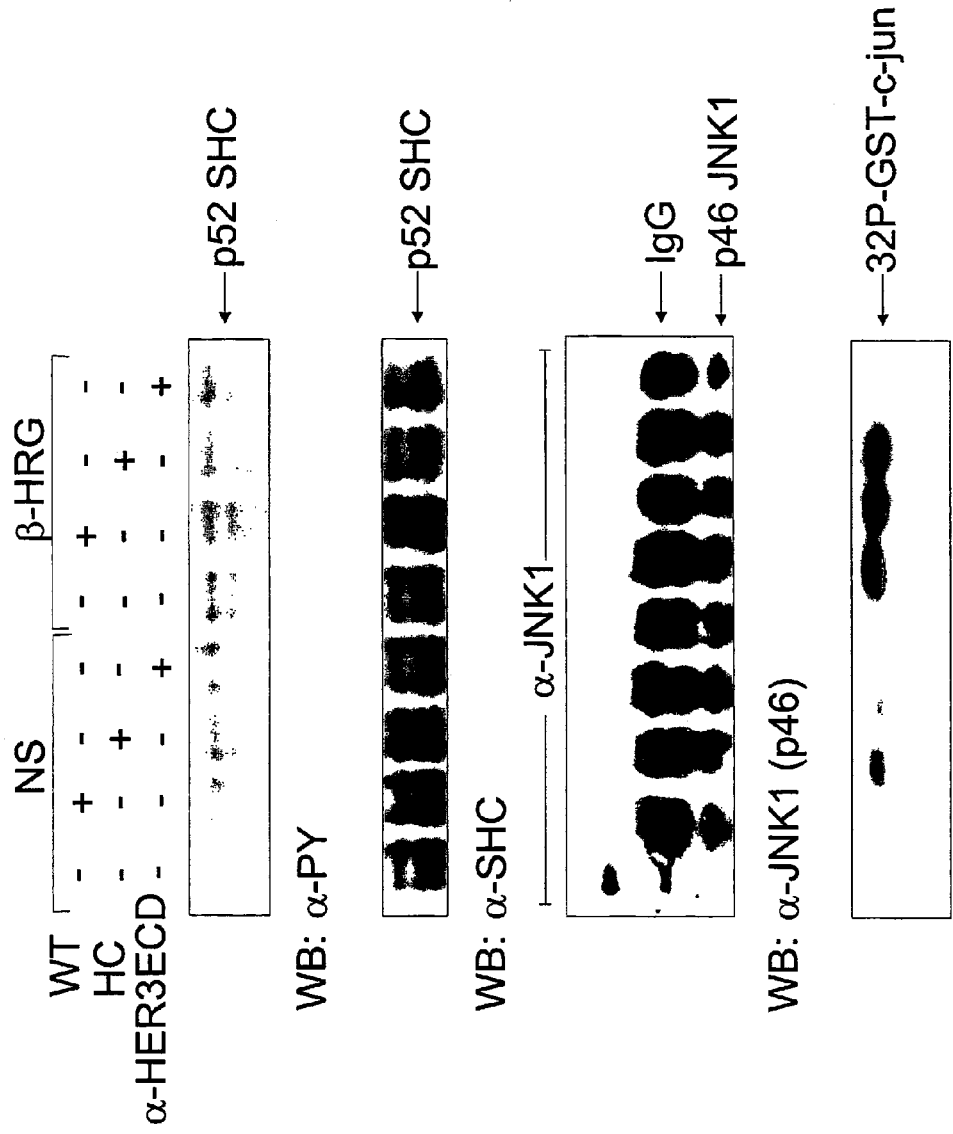
Figure 3:
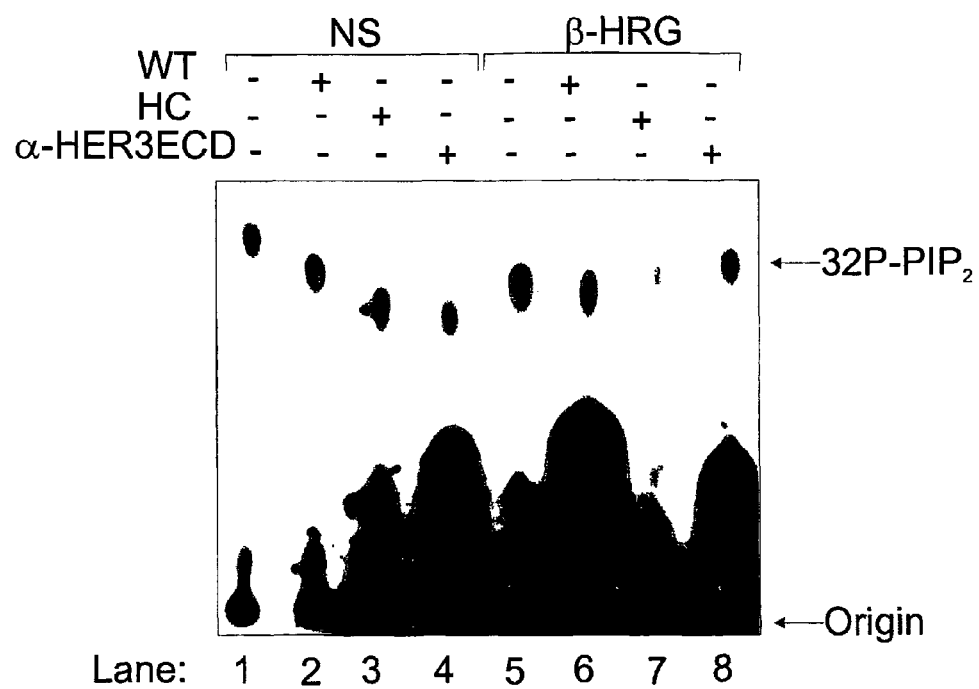
Figure 3C:
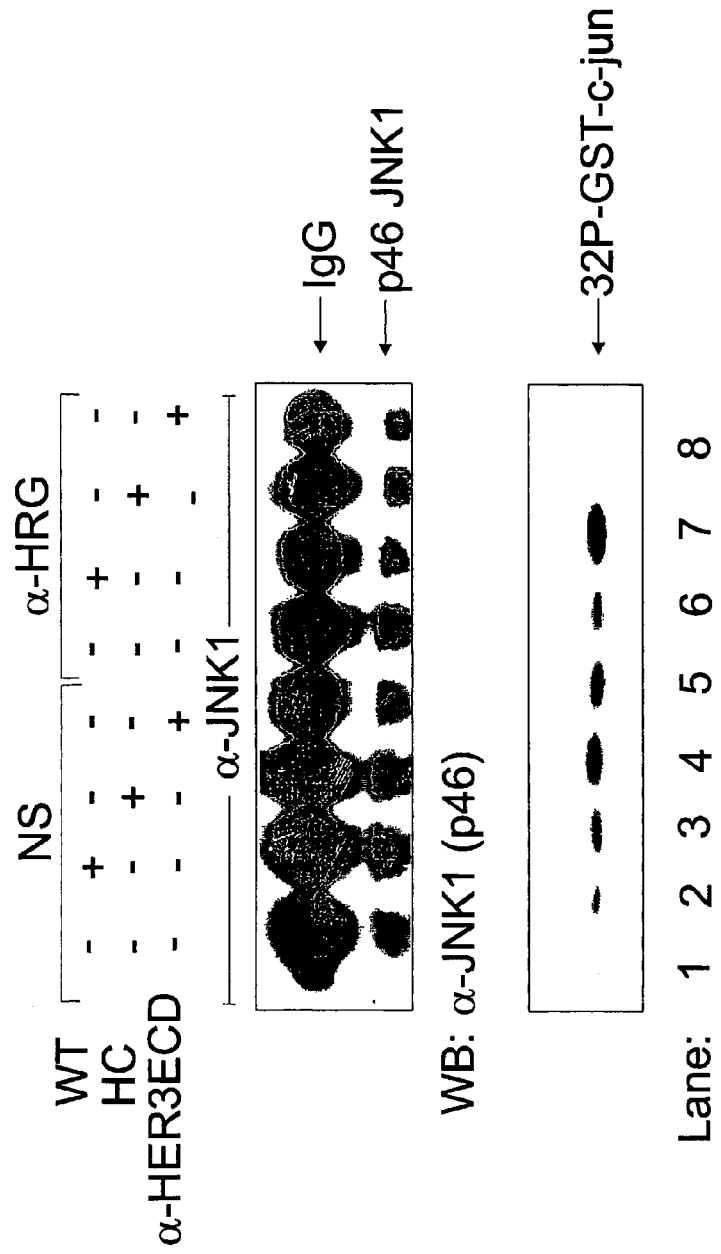

The adaptor protein SHC mediates MAPK signalling pathways downstream of growth-factor receptors, activating ERK2 and JNK, respectively. To investigate the effect of α-HER3$^{ECD}$ on ERK2 and JNK, we performed MAPK kinase assays under the same experimental conditions in MCF-7 and MB-468 (FIG. 3). We observed a strong decrease of JNK activity in all cell lines, but an equivalent effect of HC on JNK was only detectable in MCF-7 (FIG. 3a). ERK2 activity was only slightly but significantly decreased through α-HER3$^{ECD}$, whereas HC had no effect on ERK2 activity (data not shown). Since an involvement of PI$_3$-K in carcinoma invasion has recently been demonstrated, we investigated the inhibitory properties of α-HER3 on PI$_3$-K activity and carried out PI$_3$-K assays (FIG. 3). In MCF-7 and MDA-MB-486 PI$_3$-K activity was strongly reduced in comparison to HRG-treated cells (FIG. 3a, b). In MDA-MB-486 HC possessed an even greater effect on PI$_3$-K activity than α-HER3$^{ECD}$. These data suggest that α-HER3$^{ECD}$ downregulates JNK and PI$_3$-K activity, respectively, in MCF-7 and MDA-MB-486 cells.

4. α-HER3$^{ECD}$ Enhances Endocytotic Downregulation of HER3

Figure 4A:
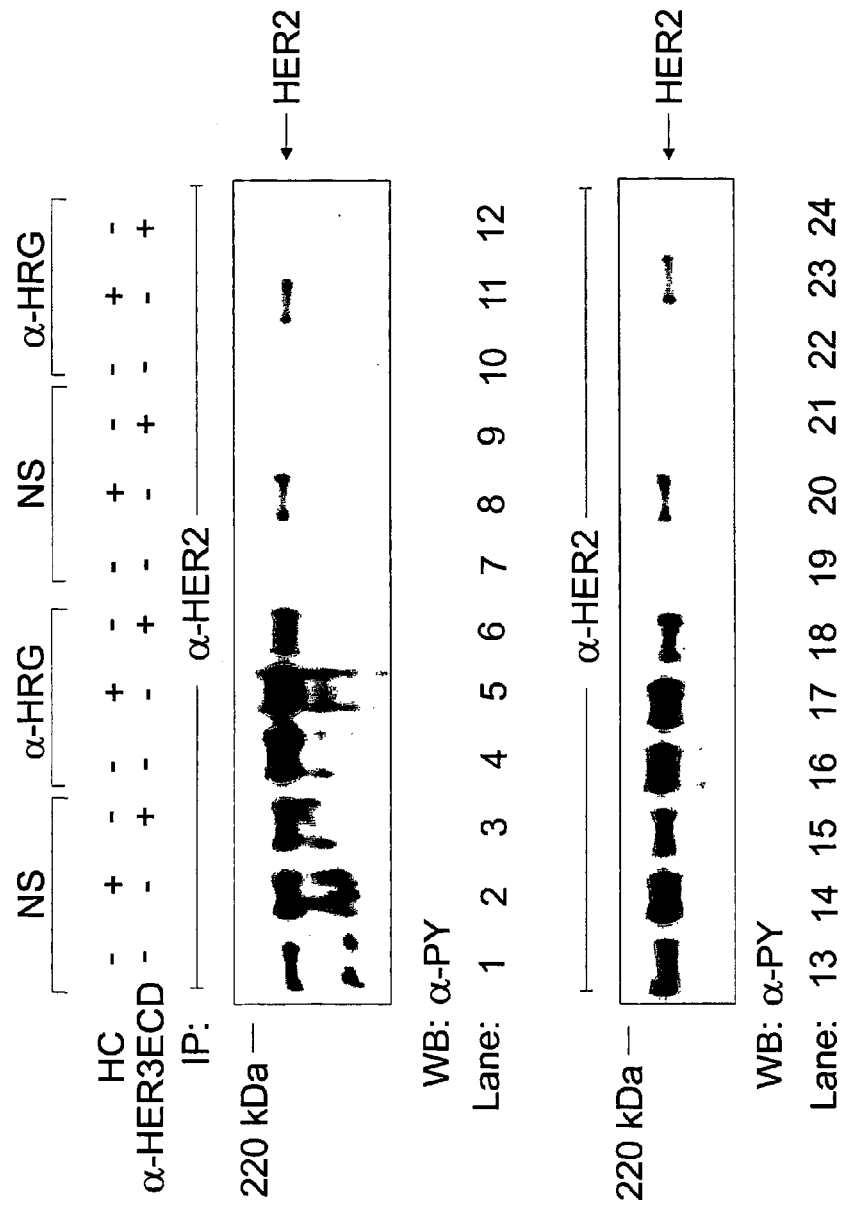
FIG. 4A depicts immunoprecipitation of MCF-7$^{ADR}$ cells with α-HER2 (upper panel) and probed with α-PY (lower panel).
Figure 4B:
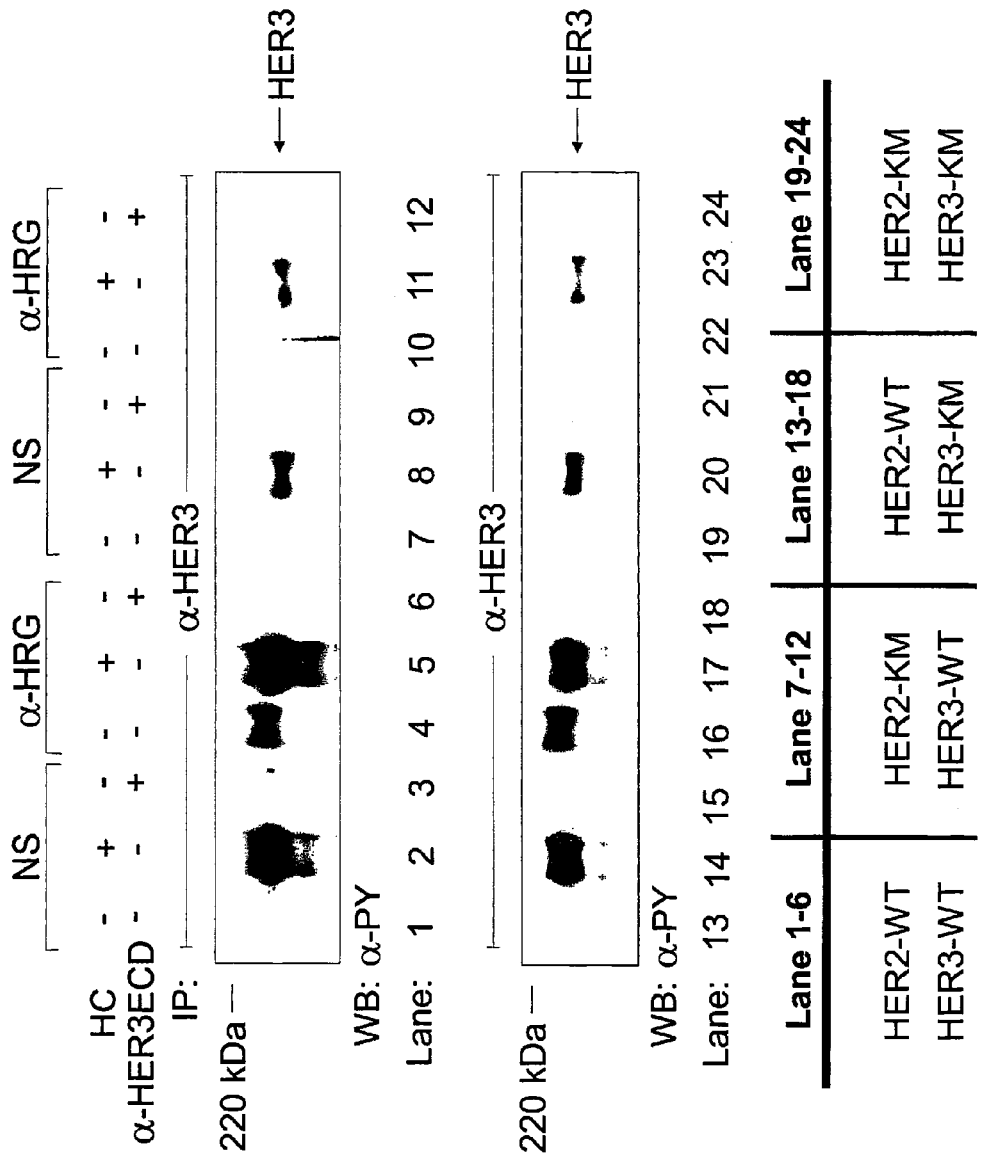
FIG. 4B depicts immunoprecipitation of MCF-7$^{ADR}$ cells with α-HER3 after pretreatment with α-HER3$^{ECD}$ (upper panel). Whole cell lysates (WCL) were probed with α-PY as a control (lower panel).
Figure 5A:
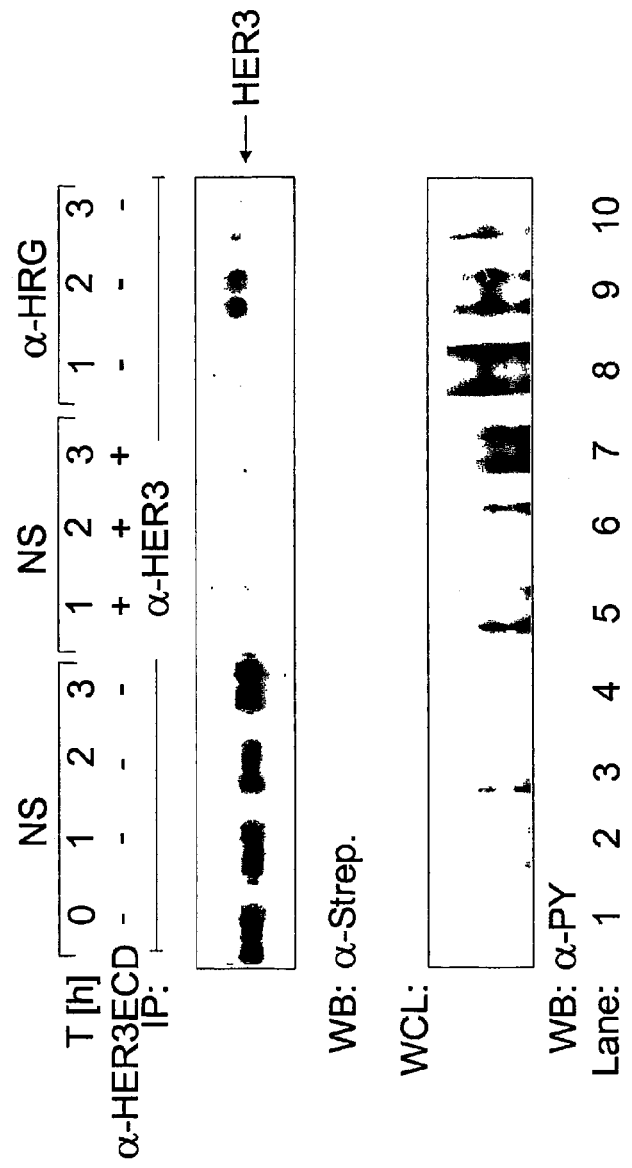
FIG. 5A depicts the results of a time course experiment for the effect of α-HER3$^{ECD}$ and HC on the endocytosis of HER3 in MCF7$^{ADR}$ cells stimulated with HRG. Cell lysates were immunoprecipitated with α-HER3. Tyrosine phosphorylation level of whole-cell lysates was analyzed by Western blot with anti-PY MAb.
Figure 5B:
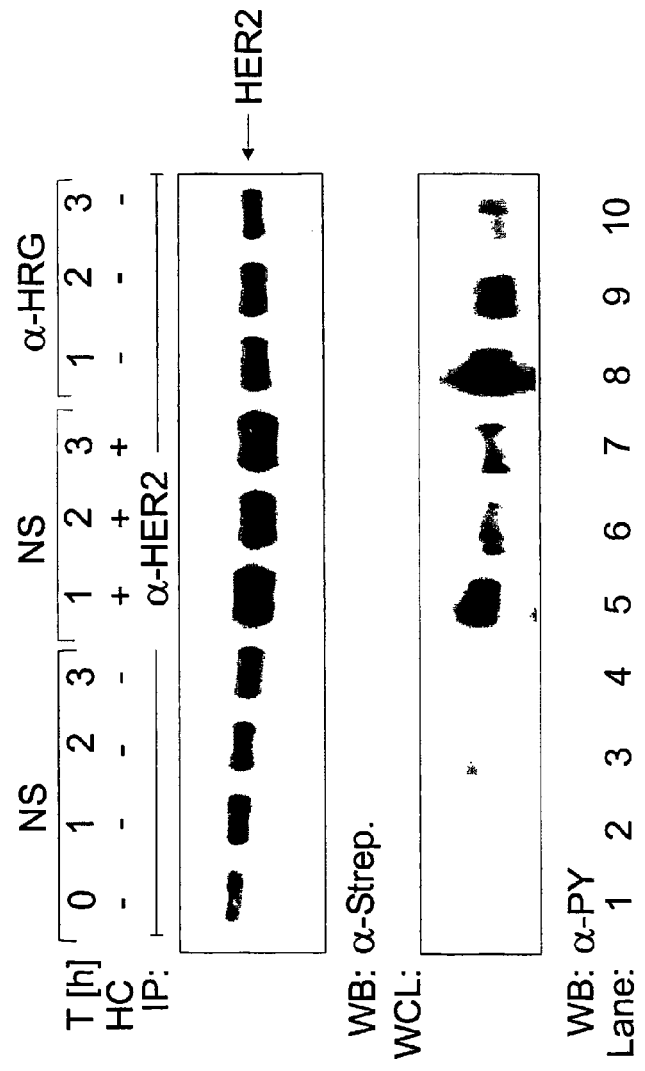
FIG. 5B depicts the results of a time course experiment for the effect of α-HER3$^{ECD}$ and HC on the endocytosis of HER2 in MCF7$^{ADR}$ cells stimulated with HRG. Cell lysates were immunoprecipitated with α-HER2. Tyrosine phosphorylation level of whole-cell lysates was analyzed by Western blot with anti-PY MAb.

HER2 and HER3 are endocytosed and recycled after HRG stimulation. We were interested in establishing whether α-HER3$^{ECD}$-mediated inhibition of HER3 tyrosyl-phosphorylation originates from accelerated endocytosis. To gain insight, we performed a time course with MCF-7 cells in the absence or presence of α-HER3$^{ECD}$ or HRG, respectively, and stimulated subsequently with HRG (FIG. 4). HER3 was then immunoprecipitated after biotinylation of the membrane proteins. We observed that HER3 is endocytosed rapidly after pretreatment with α-HER3$^{ECD}$ (FIG. 4b upper panel). Applying HRG to the cells had the same effect, with the difference that after two hours HER3 was exported back to the membrane and after three hours it was endocytosed again. As a control, whole cell lysates (WCL) were probed with PY (FIG. 4b lower panel). In comparison to HRG-treated cells where the content of tyrosyl-phoshorylated protein was diminished after three hours, accelerated endocytosis of HER3 occurred after one hour of pretreatment with α-HER3$^{ECD}$. To compare α-HER3$^{ECD}$ with HC we performed the same experiment with HC and immunoprecipitated HER2 (FIG. 4a upper panel). Strikingly, HER2 was not endocytosed after pretreatment with HC at any time point, whereas HRG lead to rapid endocytosis. When endocytosed receptors and whole cell lysates, probed with anti-phosphotyrosine (PY) are compared, it clearly appears that the phosphotyrosine content decreased with α-HER3$^{ECD}$, but not with HC (FIG. 4b lower panel). Our data indicate that α-HER3$^{ECD}$ downregulates HER3 rapidly through accelerated endocytosis, thus rendering the cell insensitive to HRG stimulation.

5. α-HER3$^{ECD}$ Inhibits Migratory and Proliferative Properties of Breast Cancer Cell Lines In order to assess the biological function of α-HER3$^{ECD}$ on the migratory and proliferative properties of breast cancer cells, we performed BrdU-incorporation assays in the presence or absence of α-HER3$^{ECD}$ and stimulated with HRG. Pretreatment with α-HER3$^{ECD}$ decreased proliferation by 28.7%±6.18% and 21.1%±7.62% in MCF-7 and MDA-MB-486, respectively. The observed inhibition in proliferation correlated with the ERK2 assays, whereas HC had no effect in these cell lines (data not shown). Furthermore, to investigate the effect of α-HER3$^{ECD}$ on the migratory properties of breast cancer cells, we conducted chemotaxis experiments with MCF-7 and MDA-MB-486 in the presence or absence of α-HER3$^{ECD}$. We observed a strong decrease in migration of 59.1% (P=0.018) and 55.4% (P=0.00005) in MCF-7 and MDA-MB-486, respectively. In addition, migration could also be inhibited in MDA-MB231 by 35%, but with a lesser significance (P=0.06). Our data clearly show an inhibitory effect of α-HER3$^{ECD}$ on proliferation and migration in MCF-7 and MDA-468.

6. Generation of Monoclonal Antibodies Against HER3

We generated then murine monoclonal antibodies against the extracellular domain of HER3, immunizing Balb/c mice with a human recombinant fusion protein of the extracellular part of HER3 and a C-terminal His-Tag (HER3-6×His-CT). The immunogen was obtained by transfection, selection with G418 and stable expression of the construct in HEK293 cells; the cell culture supernatant of the clone with the highest expression level was collected and the protein purified after ammonium sulfate precipitation, dialysis and subsequent metal ion affinity chromatography (Ni-NTA). Quality assurance was accomplished by Western blotting (data not shown). Immunization was performed by intraperitoneal injection with 22 μg of HER3-6×His-CT according to the manufacturer's protocol (Qiagen ImmunEasy Mouse Adjuvant). Hybridoma cell lines producing monoclonal antibodies were generated using standard methods.

7. Monoclonal Antibodies Against HER3 Preferentially Bind to its Protein Backbone and have Different Effects on the Endocytic Processes of HER3

We identified by FACS analysis three monoclonal antibodies recognizing specifically native HER3 on the cell surface of MCF-7 cells (data not shown). 1B4C2 and 1B4C3 are IgG2a isotype antibodies, whereas 2D1D12 is an IgG1 isotype antibody. No cross-reactivity with the other members of the EGFR family was detected (data not shown). We then wanted to determine whether the antibodies bind to glycosylated structures or to the protein backbone of HER3 and which consequences this would have on the endocytic regulation of the receptor. Therefore we pretreated MCF-7 cells in the presence or absence with the antibiotic Tunicamycin for 16 h, which is known to prevent N-linked glycosylation of cell surface proteins. After lysing the cells we immunoprecipitated HER3 with the monoclonal antibodies 2F12 (directed against the intracellular part of HER3), α-HER3$^{ECD}$ (extracellular part of HER3), 1B4C2, 1B4C3 and 2D1 D12. Our data show that α-HER3$^{ECD}$, 1B4C3 and 2D1D12 all bind preferentially to the protein backbone of HER3, whereas 1B4C3 also has an affinity to glycosylated forms of HER3 (FIG. 6A).

To investigate the effect of 1B4C3 and 2D1D12 on the endocytic processes of HER3, we performed a time-course experiment, wherein MCF-7 cells where incubated for various time periods with 1B4C3 or 2D1D12, respectively. The cell surface proteins were biotinylated, precipitated with an antibody against the intracellular domain of HER3 and probed against streptavidin. We observed that 1B4C3 accelerates the endocytosis of HER3 similarly to α-HER3 ECD, whereas 2D1D12 stabilized and therefore accumulated HER3 on the cell surface (FIG. 6B).

8. Monoclonal Antibodies 1B4C3 and 2D1D12 Inhibit Downstream Signals of HER3 and HER2

Figure 6C:
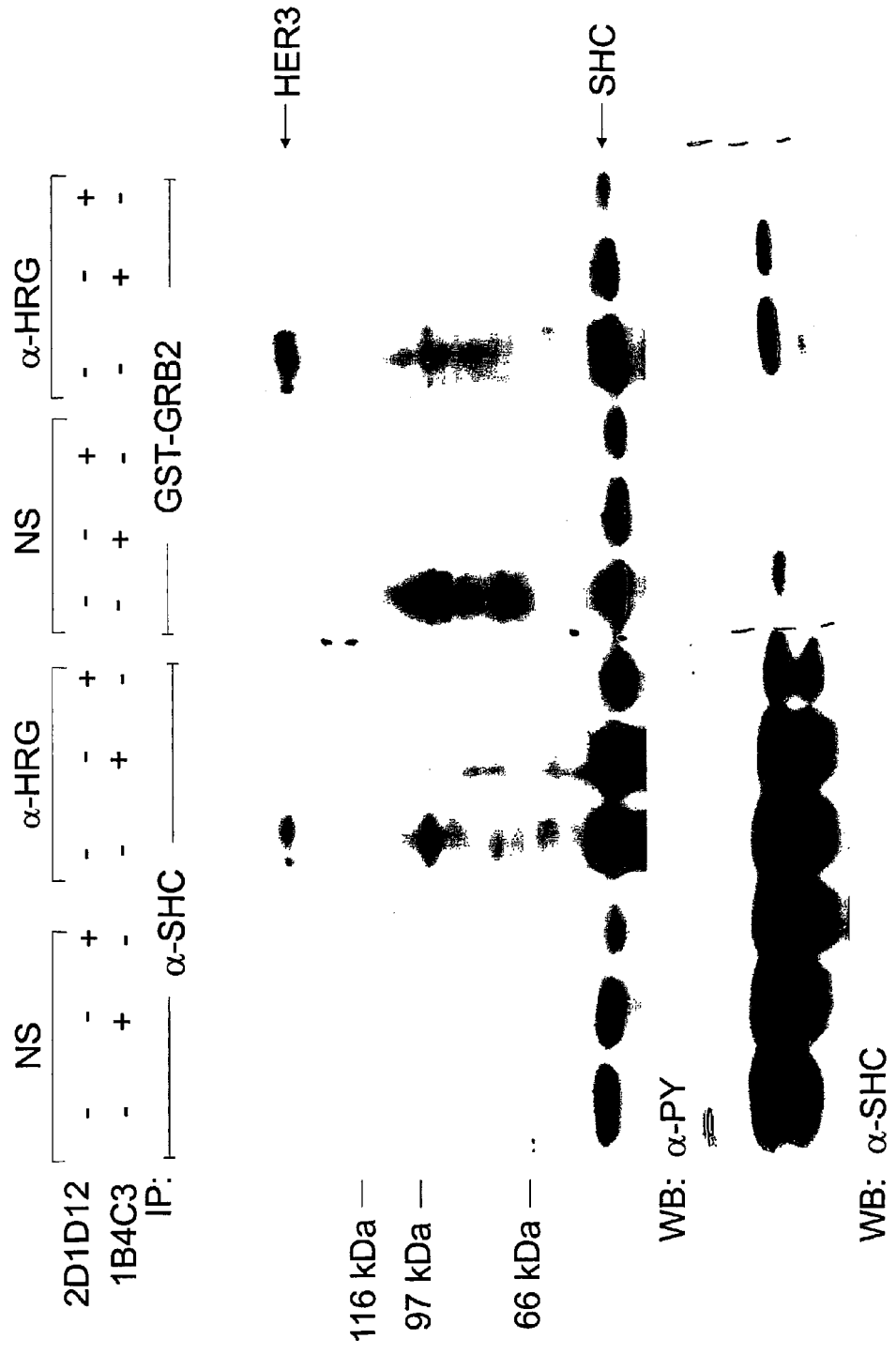
FIG. 6C shows immunoprecipitation of MCF7 cells untreated or pretreated with 1B4C3 and 2D1D12 using α-SHC and a parallel GST-GRB2 pulldown untreated or pretreated with the antibodies. The cell lysates were probed by Western blot with α-PY and α-SHC.

We then asked whether 1B4C3 and 2D1D12 could inhibit tyrosine phosphorylation of HER2 and of the HER3 substrate SHC. Since GRB2-binds to HRG-stimulated HER2 and transmits in the same way as SHC mitogenic signals to the MAPK pathway, we immunoprecipitated SHC and in parallel performed a GST-GRB2 pulldown in MCF-7 cells untreated or pretreated with the antibodies and subsequently stimulated with HRG (FIG. 6C). This experiment shows that both antibodies inhibit tyrosine phosphorylation of SHC and the association of GRB2 with SHC. Furthermore, the antibodies inhibit the association of SHC with HER3 and the heterodimerization between HER2 and HER3. These data show that downstream signalling is inhibited by 1B4C3 and 2D10D12, albeit with 2D1D12 having an even stronger inhibitory effect than 1B4C3.

Figure 7:
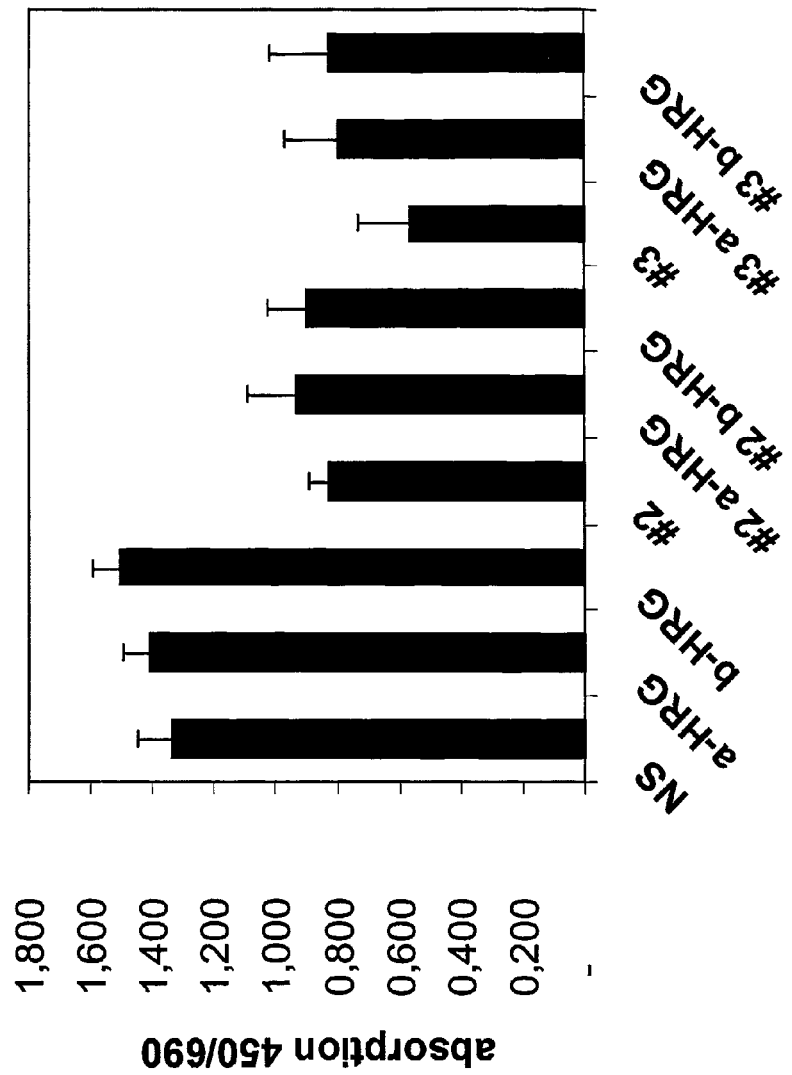
FIG. 7 shows the results of BrdU-incorporation assays in the presence or absence of the antibodies for Mel Gerlach, MDA-MB 435, and ZR 75-1 cell lines.
Figure 7:
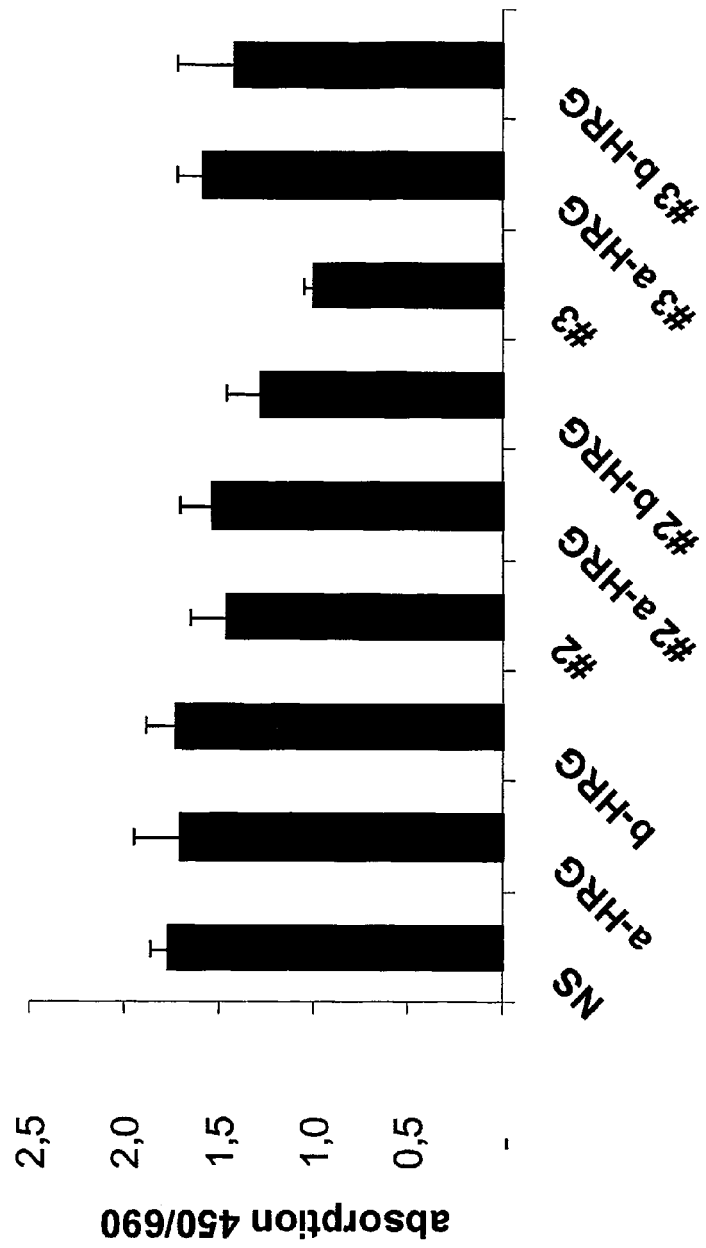
Figure 7:
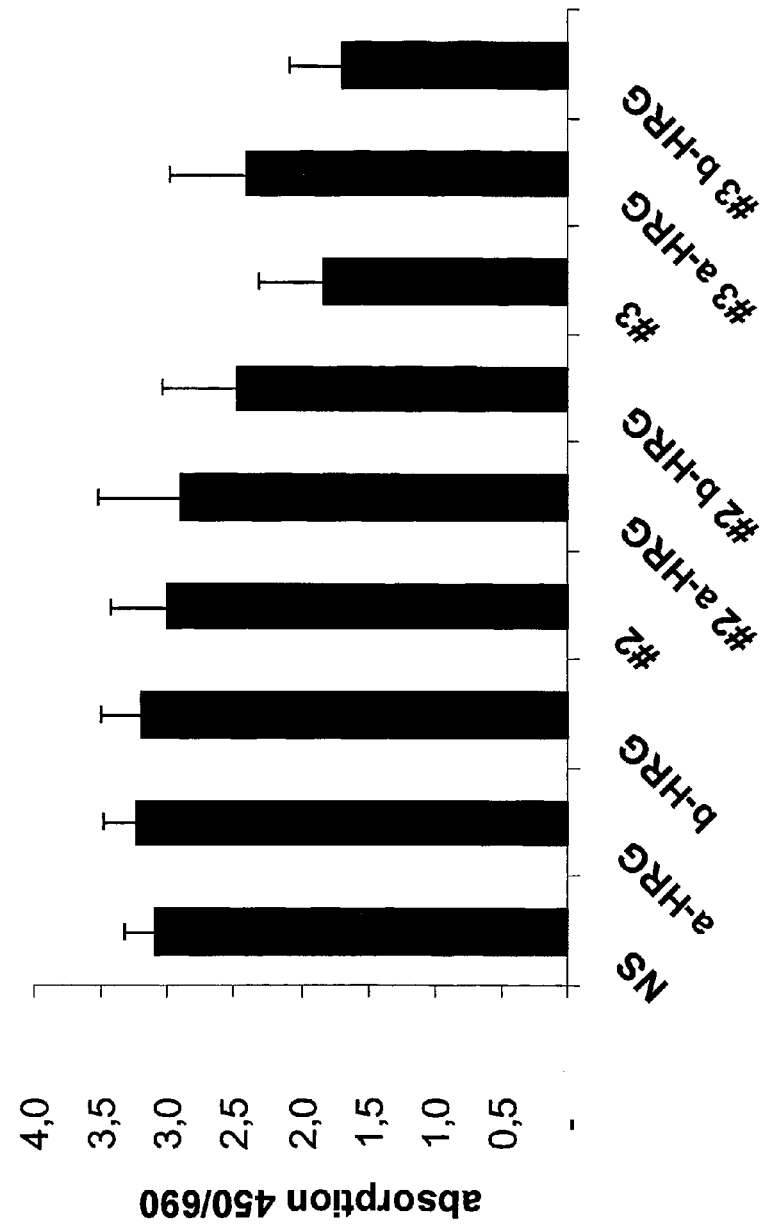

9. Monoclonal Antibody 2D1D12 Inhibits Proliferation of Breast Cancer Cell Lines MDA-MB-435S, ZR-75-1 and Melanoma Cell Line Mel Gerlach We next set out to explore the biological activity of 1B4C3 and 2D1D12 in the two breast cancer cell lines MDA-MB-435S (ATCC HTB-129), ZR-75-1 (ATCC CRL-1500) and the melanoma cell line Mel Gerlach (Klinikum Großhadern, Munich). We have chosen the cell lines due to their tumorigenicity in nude mice and their high HER3 expression level. It should be noted that melanoma cells overexpress HER3, since HER3 is critical in the development of melanocytes as well as oligodendrocytes. To test our hypothesis that 1B4C3 and 2D1D12 abrogate mitogenic signals and consequently the proliferative properties of cancer cells, we performed BrdU-incorporation assays in the presence or absence of the antibodies (FIG. 7). Proliferation was strongly reduced in all cell lines by 2D1D12, whereas 1B4C3 had only an inhibitory effect in Mel Gerlach. Taken together, our data constitute the first evidence that monoclonal antibodies against HER3 could be potentially regarded as new therapeutic weapons against cancer.

The hybridoma cell lines producing antibodies 1B4C3 and 2D1D12 were deposited on Aug. 7, 2001 and Jul. 24, 2001, respectively, at DSMZ.

10. Effect of HER3 Antibodies on Signal Transduction

10.1. Methods

MDA-MB-435S were obtained from ATCC (HTB-129) and Mel-Juso were obtained from Cell Lines Servive (CLS) (0282-HU). GST-p85 (a.a 333-430) was obtained from Santa Cruz. GST-GRB2 was purified as described previously. Phospho-AKT (P-Ser 473) was from New England Biolabs (NEB). HER2 antibody was purified as described from the hybridoma culture supernatent (ATCC CRL-10463). For GST-pull-down assays 1.25 µg bait protein was used. BrdU-Incorporation and invasion assays were performed as previously described. All experiments were performed at least two times.

10.2. Results and Discussion

Figure 8:
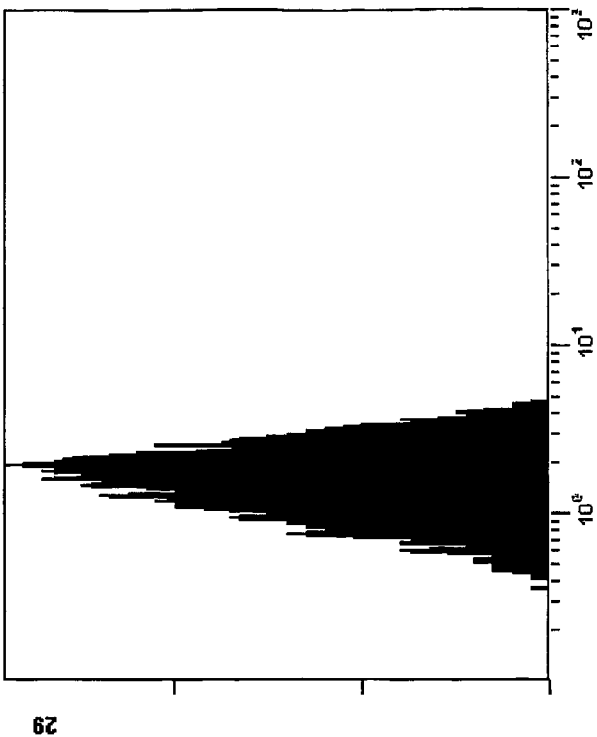
FIG. 8A shows FACS analysis of MDA-MB-435S cells for HER2 receptors (upper panel) and HER3 receptors (middle panel). The lower panel shows a control FACS analysis using Myc.
FIG. 8B shows FACS analysis of Mel Juso cells for HER2 receptors (upper panel) and HER3 receptors (middle panel). The lower panel shows a control FACS analysis using Myc.
FIG. 8C shows a GST-pull-down assay of MDA-MB-435S cells with GST-p85 as bait and a Western blot using α-PY (upper panel), and Western blots using α-HER2, α-HER3, and α-FAK (lower panels).
FIG. 8D shows a GST-pull-down assay of Mel Juso cells with GST-p85 as bait and a Western blot using α-PY (upper panel), and Western blots using α-HER2, α-HER3, and α-FAK (lower panels).
Figure 8:
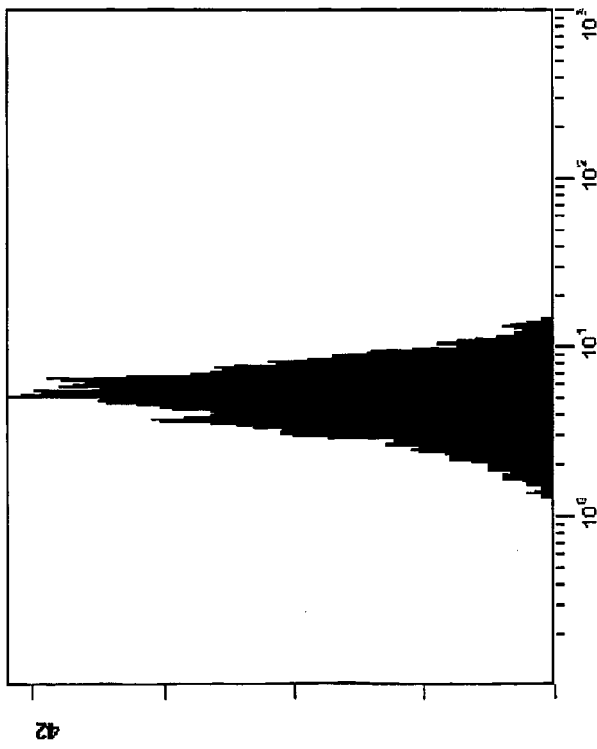
Figure 8:
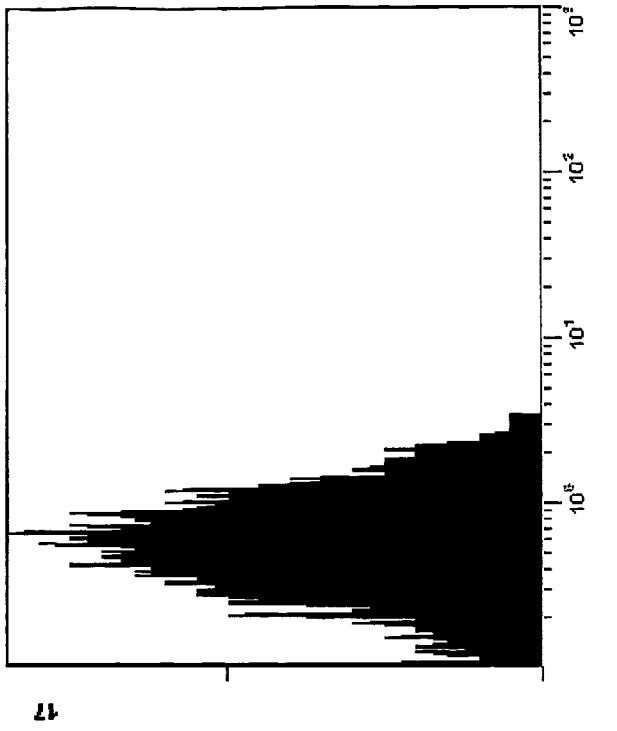
Figure 8:
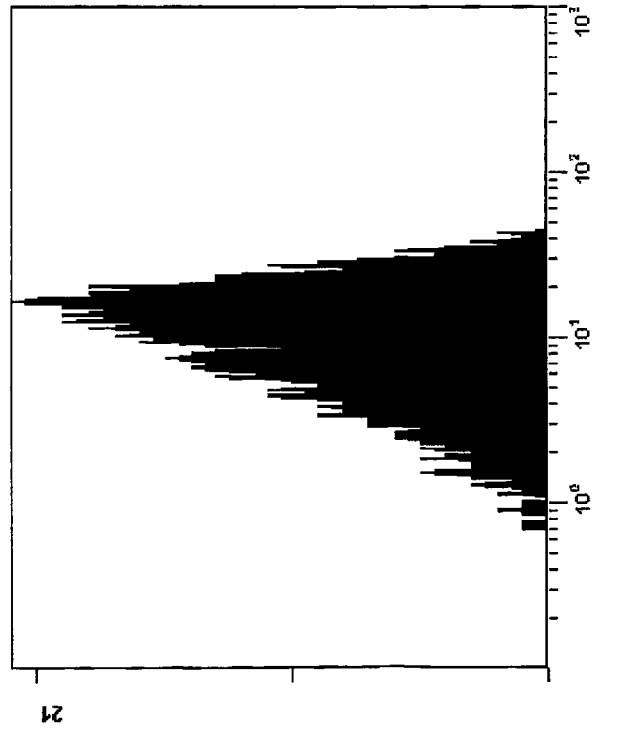
Figure 8:
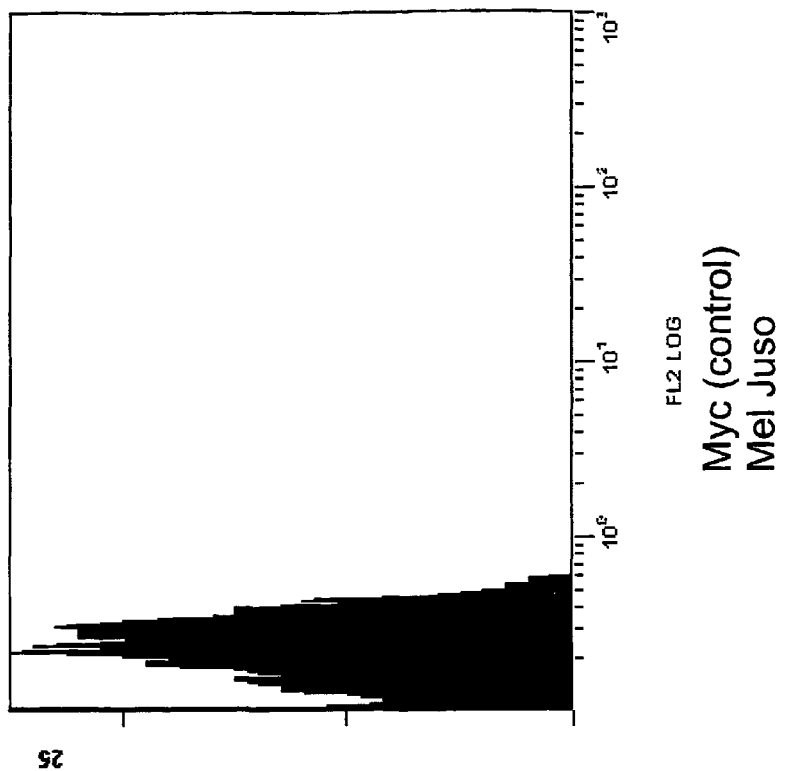
Figure 8:
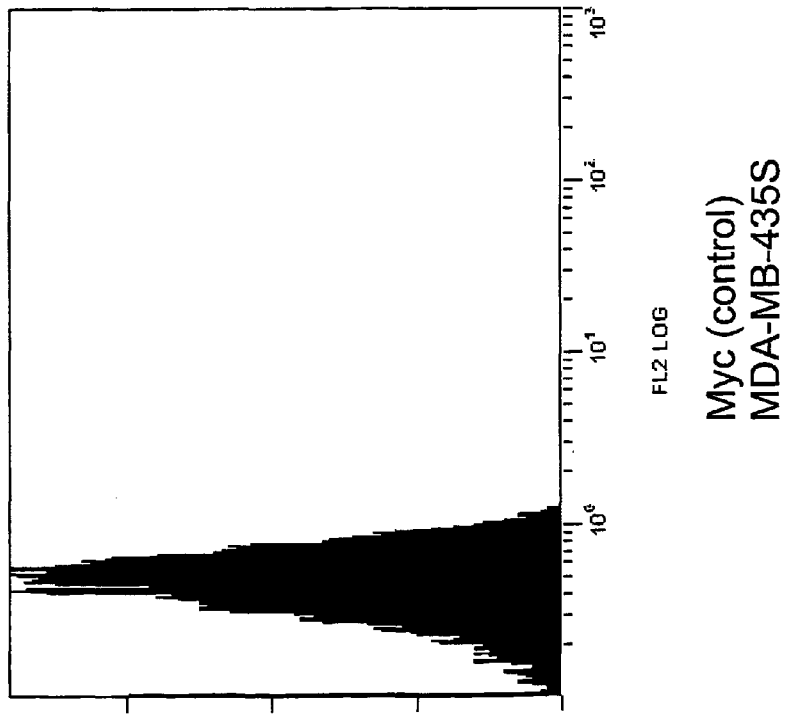
Figure 8:
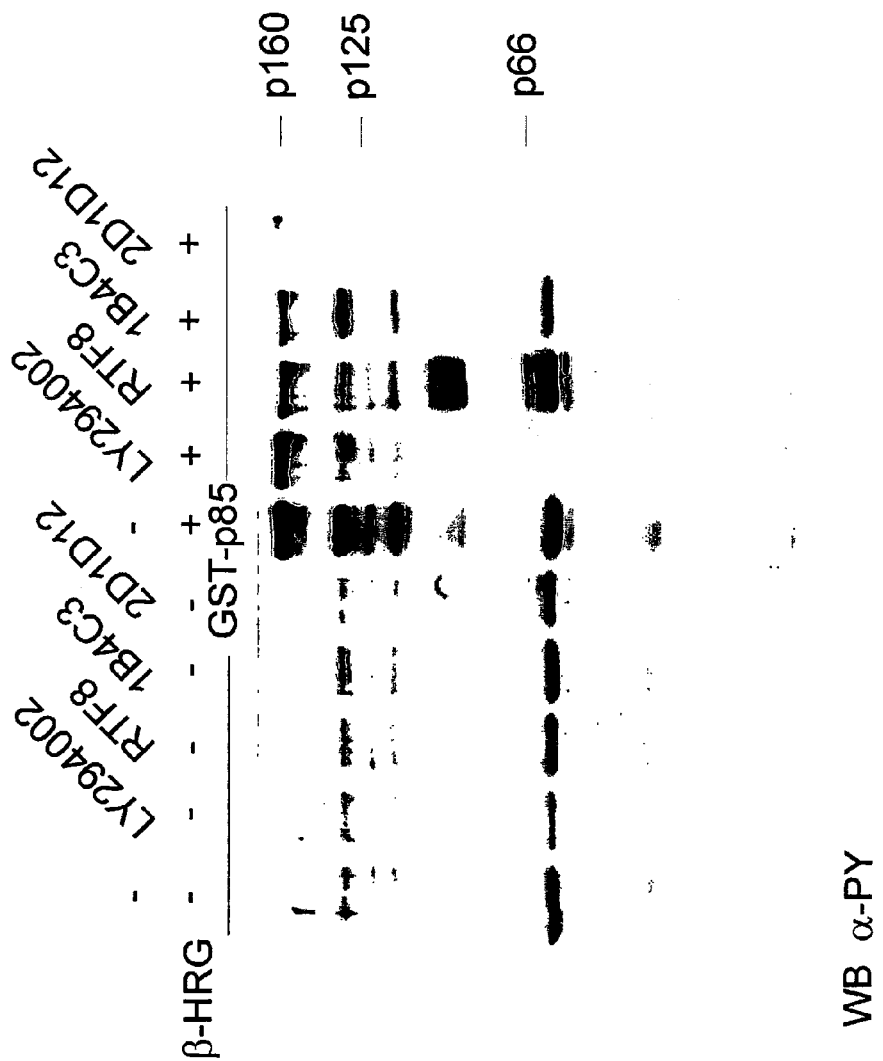
Figure 8:
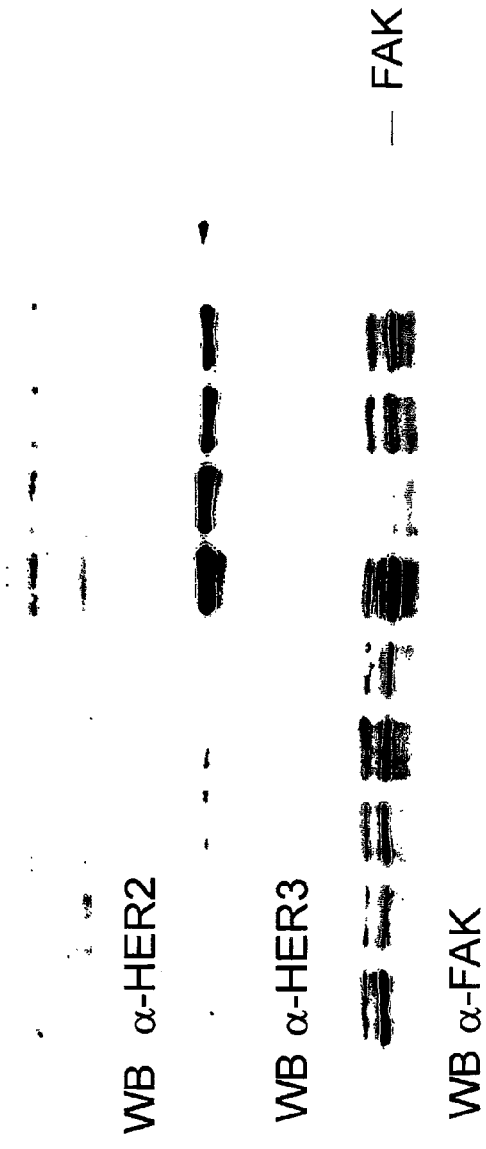

In order to examine the surface expression of HER2 and HER3 receptors in MDA-MB-435S and Mel-Juso, we additionally determined their expression level by FACS analysis (FIG. 8A, B). We observed HER2 and HER3 expression in these cell lines and went on to dissect the molecular mechanism by which HER3 antibodies act on Heregulin (HRG) mediated signal transduction. Therefore, we performed GST-pull-down assays in the human breast carcinoma cell line MDA-MB-435S and melanoma cell line Mel-Juso (FIG. 8). Quiescent cells were pretreated with HER3 antibodies 1B4C3, 2D1D12, the control anti-HER2 antibody and with PI(3)K inhibitor LY294002 and were subsequently stimulated with β-HRG. After cell lysis, protein levels were normalized and since HER3 has six potential p85 binding sites a GST-pull-down assay with GST-p85 (a.a. 0.333-430) as bait was performed. Western blot against phosphotyrosine (PY), reveals that anti-HER2 and 1B4C3 equally decrease p85 association with transactivated HER3, while LY294002 (negative control) has no inhibitory effect on p85 binding in MDA-MB-435S (FIG. 8C). However, 2D1D12 almost completely abrogates binding of p85 with HER3 in MDA-MB-435S (FIG. 8C).

Figure 8D:
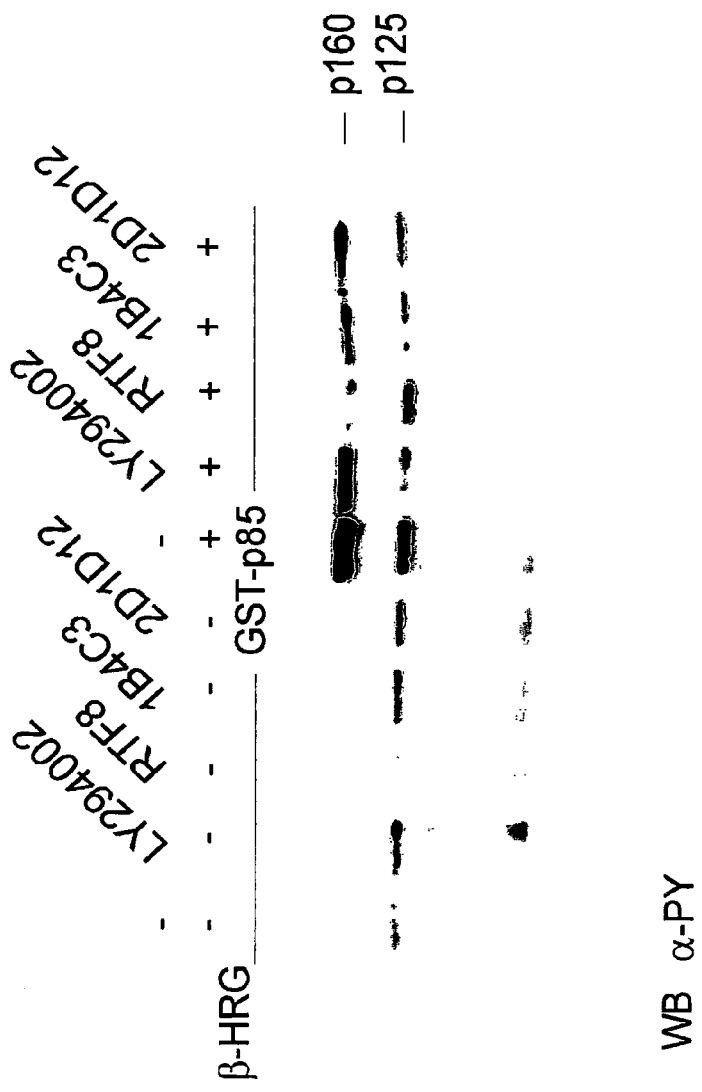
Figure 8:
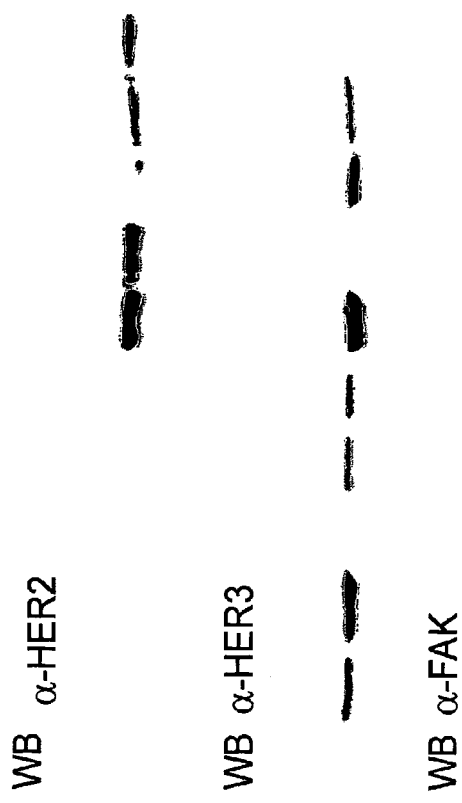

In the human melanoma cell line Mel-Juso 1B4C3 and 2D1D2 equally decrease p85 association with HER3, while anti-HER2 exhibits a more pronounced decrease in receptor association of p85 (FIG. 8D). Again, LY294002 showed no inhibitory effect on p85 binding (FIG. 8D). Moreover, we observed some prominent tyrosine phosphorylated bands in the phosphotyrosine blot at 125 kDa and 66 kDA in MDA-MD-435S and only a major band at 125 kDA in Mel-Juso. It is known that PI(3)K associates physically with focal adhesion kinase (FAK) and therefore we reprobed the blot with FAK antibodies (FIG. 8C, D lower panels). Our data show that in both cell lines only 2D1D12 and the PI(3)K inhibitor LY294002 abolished FAK association with p85. Reprobing the blot with HER2 and HER3 antibodies confirmed the diminished amount of captured HER3 and its reduced heterodimerization with HER2 (FIG. 8C, D middle panels). Taken together, our data indicate that although HER3 and HER2 antibodies decrease receptor tyrosine phosphorylation levels, they are capable of modulating different responses at the secondary level of receptor-associated effector proteins.

Figure 9:
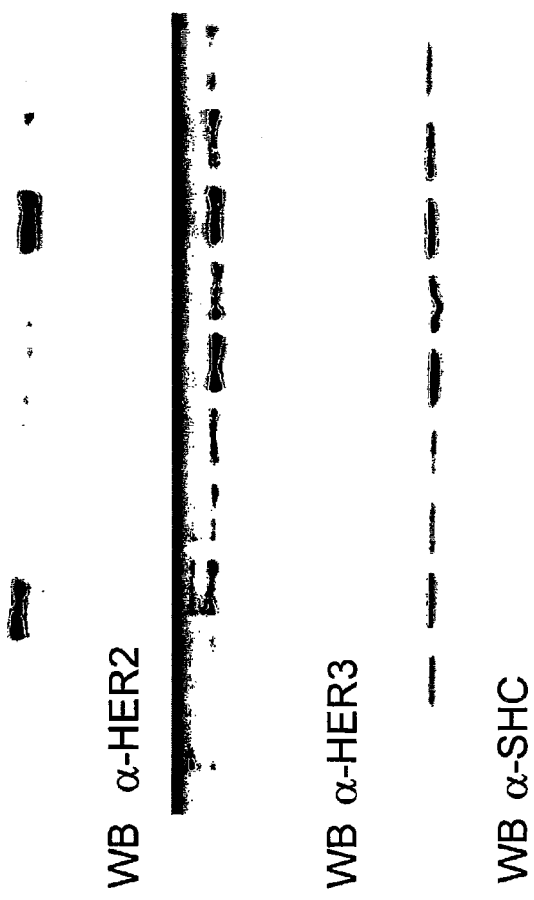
FIG. 9A shows a GST-pull-down assay of MDA-MB-435S cells with GST-GRB2 as bait and a Western blot using α-PY (upper panel), and Western blots using α-HER2, α-HER3, and α-FAK (lower panels).
FIG. 9B shows a GST-pull-down assay of Mel Juso cells with GST-GRB2 as bait and a Western blot using α-PY (upper panel), and Western blots using α-HER2, α-HER3, and α-FAK (lower panels).
Figure 9B:
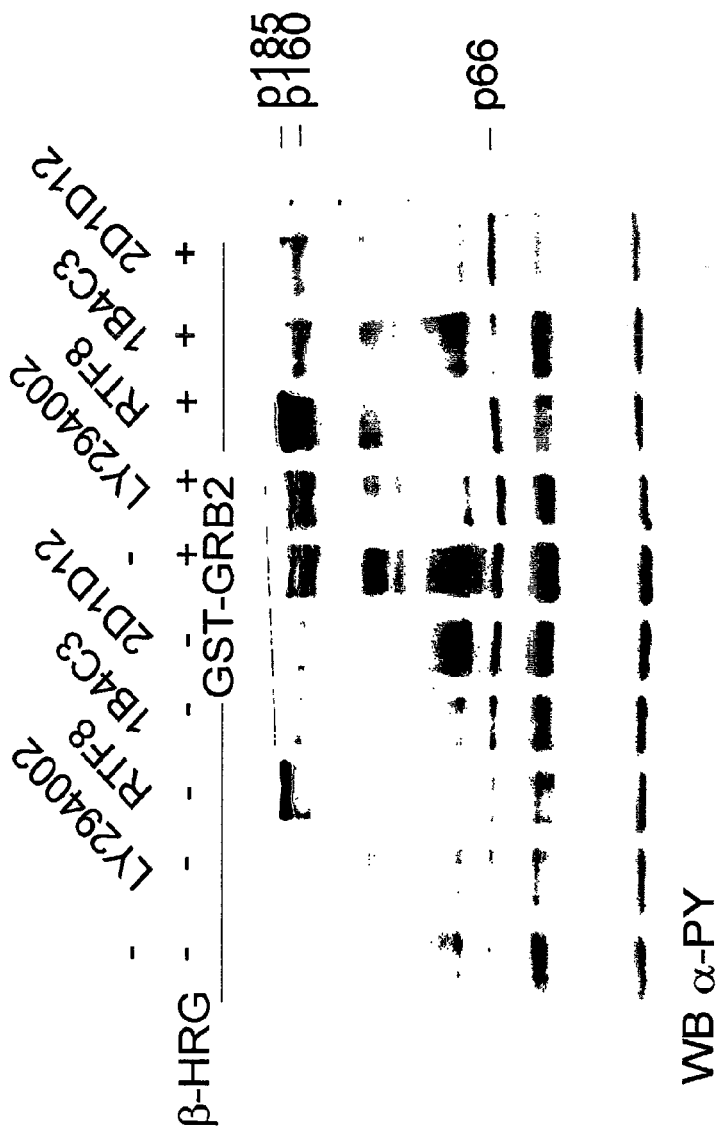
Figure 9:
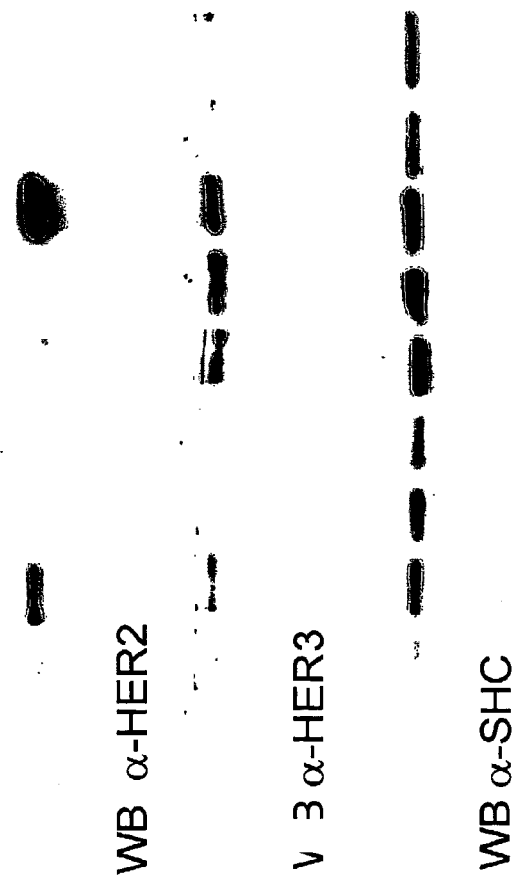

Since GRB2 only binds directly to HER2 and indirectly over SHC for HER3, we performed additional GST-pull-down experiment with GST-GRB2 as bait under identical experimental conditions and human tumor cell lines as above (FIG. 9A, B). We observed that 1B4C3 and 2D1D12 diminished receptor tyrosine phosphorylation between 160 and 185 kDa, whereas LY294002 had no inhibitory effect (FIG. 9A, B upper panel). However, pretreatment of the cells with anti-HER2 antibodies lead to increased tyrosine phosphorylation of the receptors, which could be further potentiated with β-HRG. Reprobing with HER2, HER3 and SHC antibodies show that 1B4C3 and 2D1D12 substantially inhibit GRB2 binding with HER2 and its indirect association with HER3 (FIG. 9A, B middle panels), as well as its association with SHC in both cell lines (FIG. 9A, B lower panels). On the other hand, anti-HER2 antibodies increased GRB2 binding to HER2 and SHC.

Figure 10:
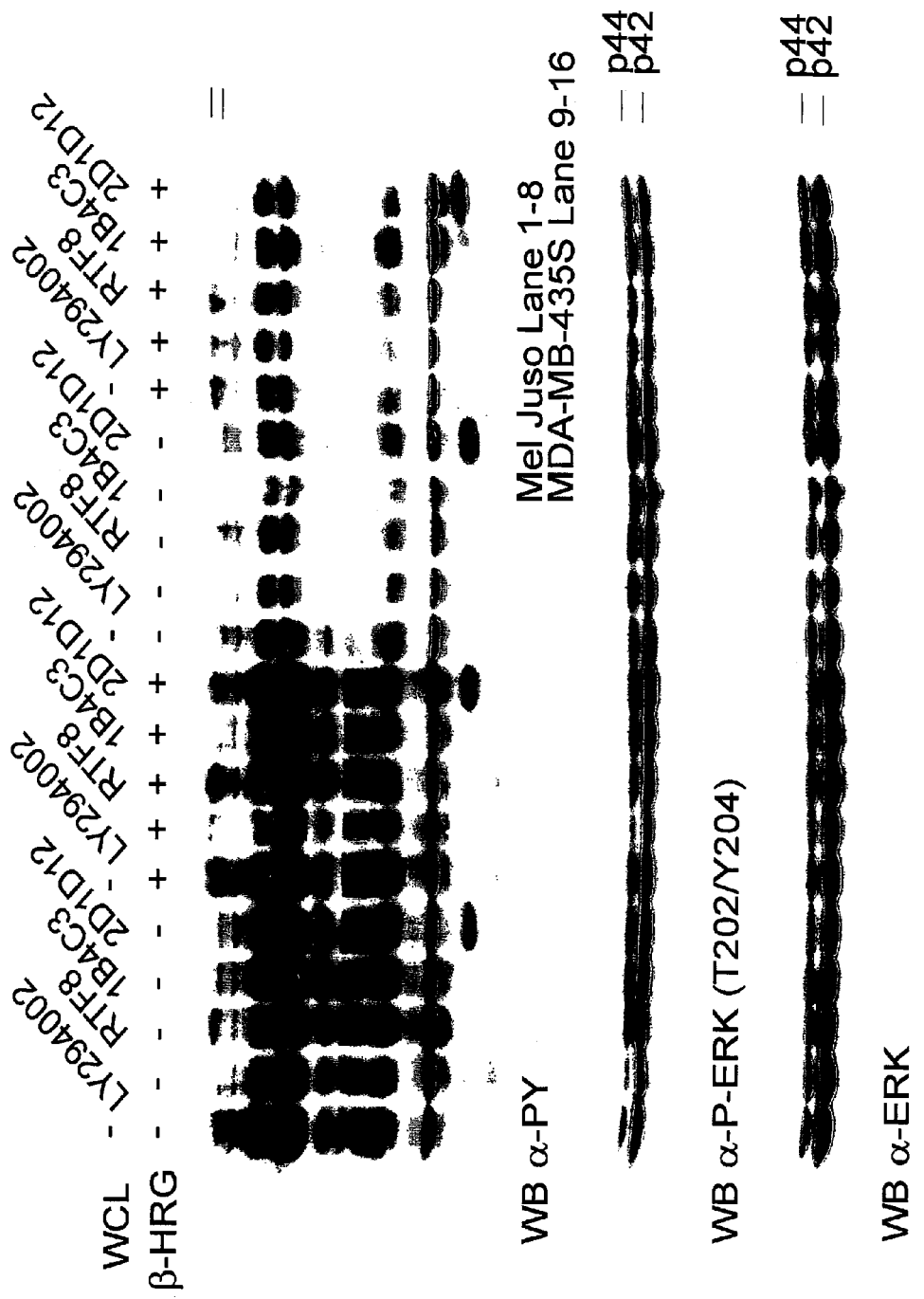
FIG. 10A shows analysis of whole cell lysates of MDA-MB-435S and Mel Juso cells in the presence or absence of antibodies (upper panel) and Western blots using α-PY, α-P-ERK, and α-ERK (middle and lower panels).
FIG. 10B shows analysis of whole cell lysates of Mel Juso cells in the presence or absence of antibodies (upper panel) and Western blots using α-P-AKT and α-SHC (middle and lower panels).
FIG. 10C shows analysis of whole cell lysates of MDA-MB-435S cells in the presence or absence of antibodies (upper panel) and Western blots using α-P-AKT (lower panel).
Figure 10:
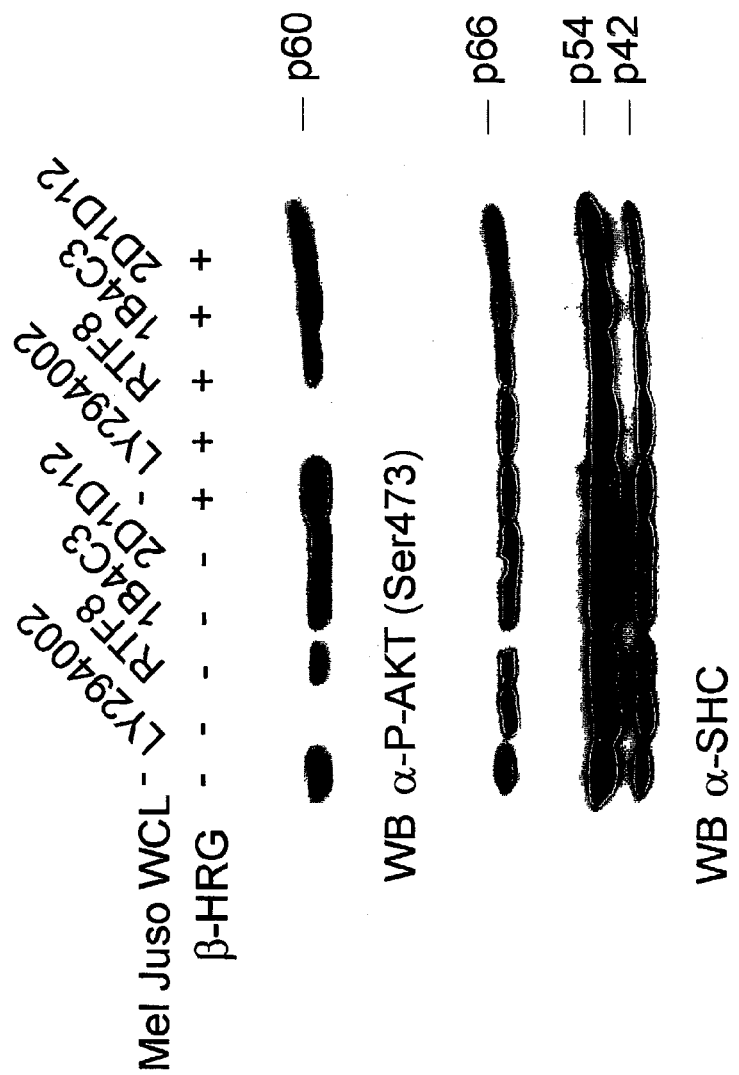
Figure 10:
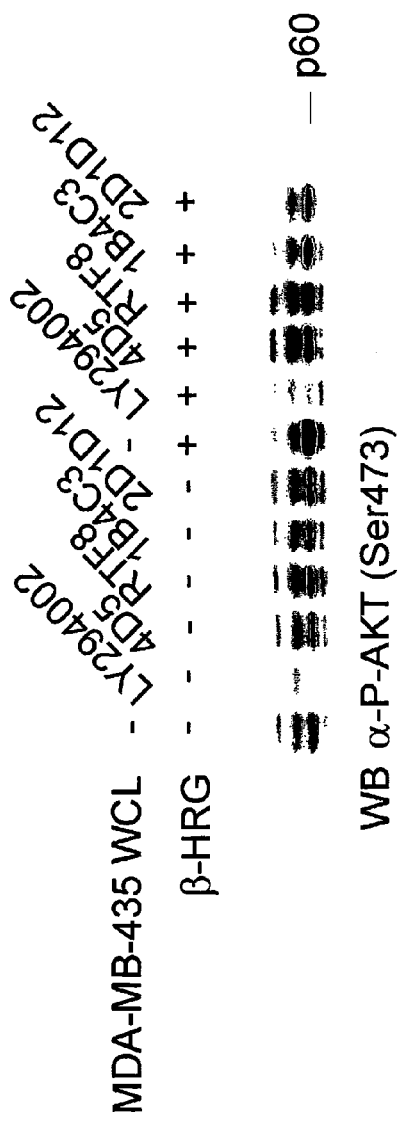

To gain more insight into antibody-mediated downstream signaling, we also analysed whole cell lysates (WCL) of the experiments described above (FIG. 10). When we looked at the phosphoprotein content of total cellular protein we observed that in both cell lines anti-HER2 constitutively activated the receptors, whereas 1B4C3 and 2D1D12 inhibited tyrosine phosphorylation of the receptors (FIG. 10A upper panel). Again LY294002 had no effect.

It is well established that HRG activates the mitogen-activated protein kinases (MAPK) pathway, leading to cell proliferation, cell survival and enhanced transcription of various genes. To examine the effect of HER2 and HER3 antibodies on HRG-induced MAPK activation, immunoblots of MDA-MB435S and Mel-Juso whole cell extracts were probed with phospho-ERK (T202/Y204) antibodies (FIG. 10). Phosphorylation of the MAPK ERK1/2 (p44/p42) showed, that despite activating the receptor, anti-HER2 slightly decreased ERK1 phosphorylation, whereas 1B4C3 and 2D1D02 had no inhibitory effect on ERK1 phosphorylation (FIG. 10A middle panel). Further reprobing the blot confirmed equal amounts of loaded protein (FIG. 10A lower panel).

Furthermore, we investigated the activation status of AKT, which is a downstream target of PI(3)K and has an important role in cell survival. We observed that anti-HER2, 1B4C3 and 2D1D12 markedly inhibited AKT phosphorylation in Mel-Juso melanoma cells (FIG. 10B upper panel). In MDA-MB-435S breast cancer cells both HER2 and HER3 antibodies significantly decreased AKT phosphorylation (FIG. 10C). LY294002 served as the positive control. This observation is of major importance, since breast cancer patients with markedly increased expression of activated AKT are more prone to relapse with distant metastasis resulting in poor clinical outcome (Perez-Tenorio G et al. British Journal of Cancer, 86, 540-545 (2002).

Figure 11:
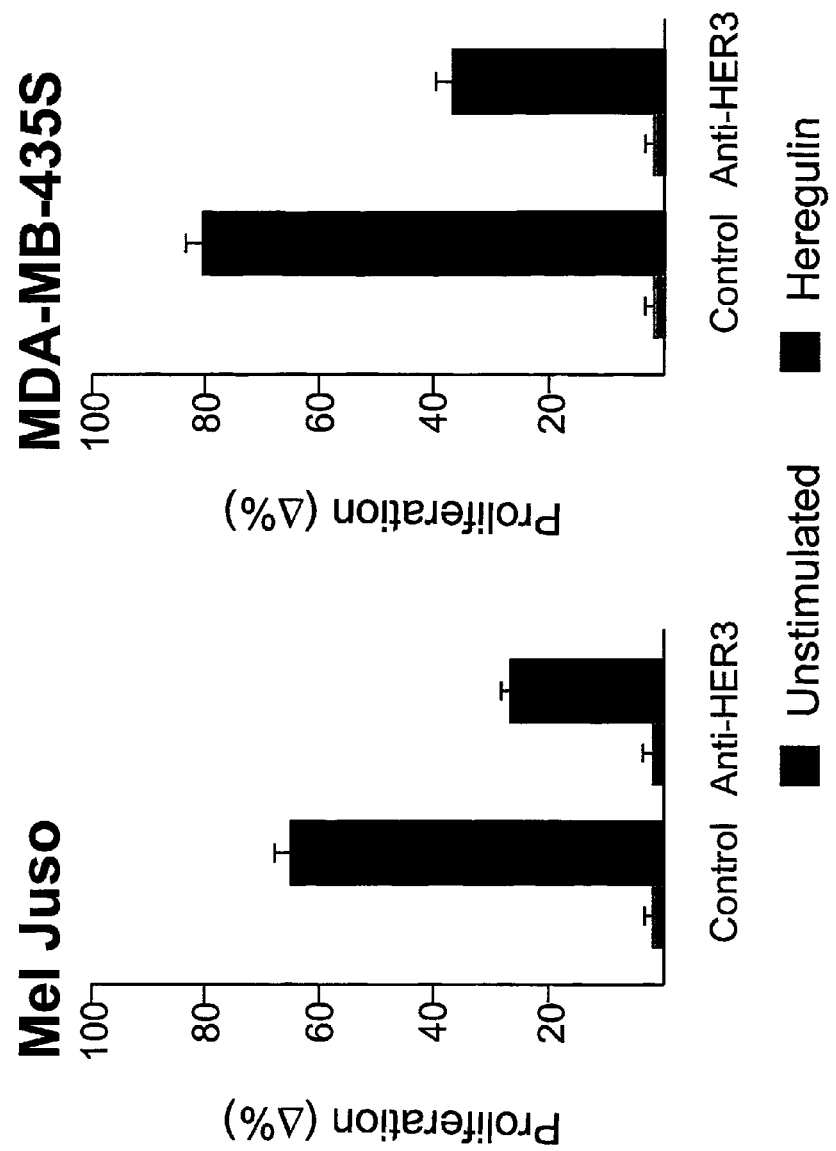
FIG. 11A shows BrdU-incorporation in Heregulin stimulated and unstimulated Mel-Juso (left panel) and MDA-MB-435S (right panel) cells pretreated with 2D1D12.
FIG. 11B shows photomicrographs of MDA-MB-435S cells that were un-stimulated or treated with antibodies.
FIG. 11C shows photomicrographs of Mel Juso cells that were un-stimulated or treated with antibodies.
Figure 11:
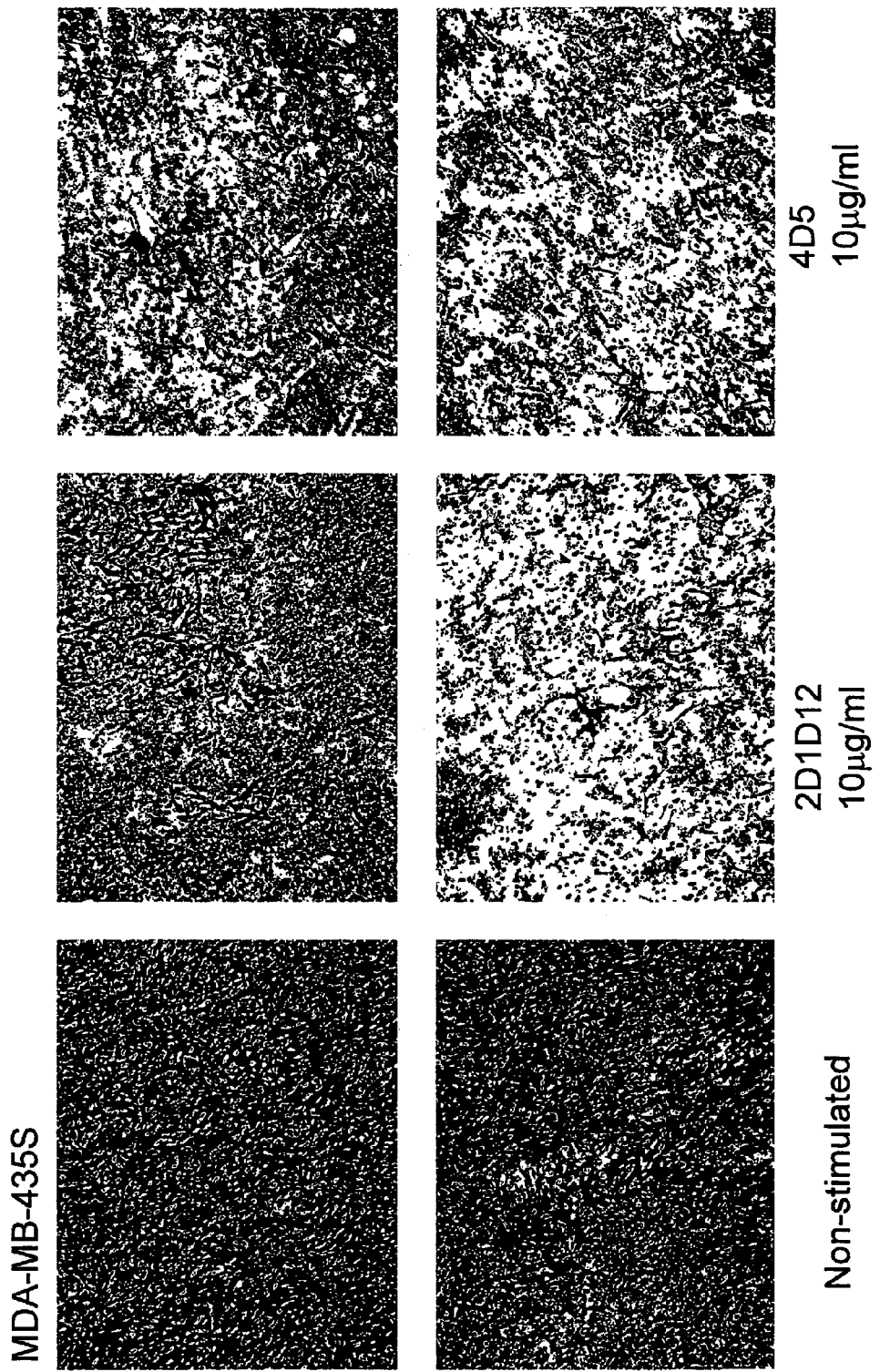
Figure 11:
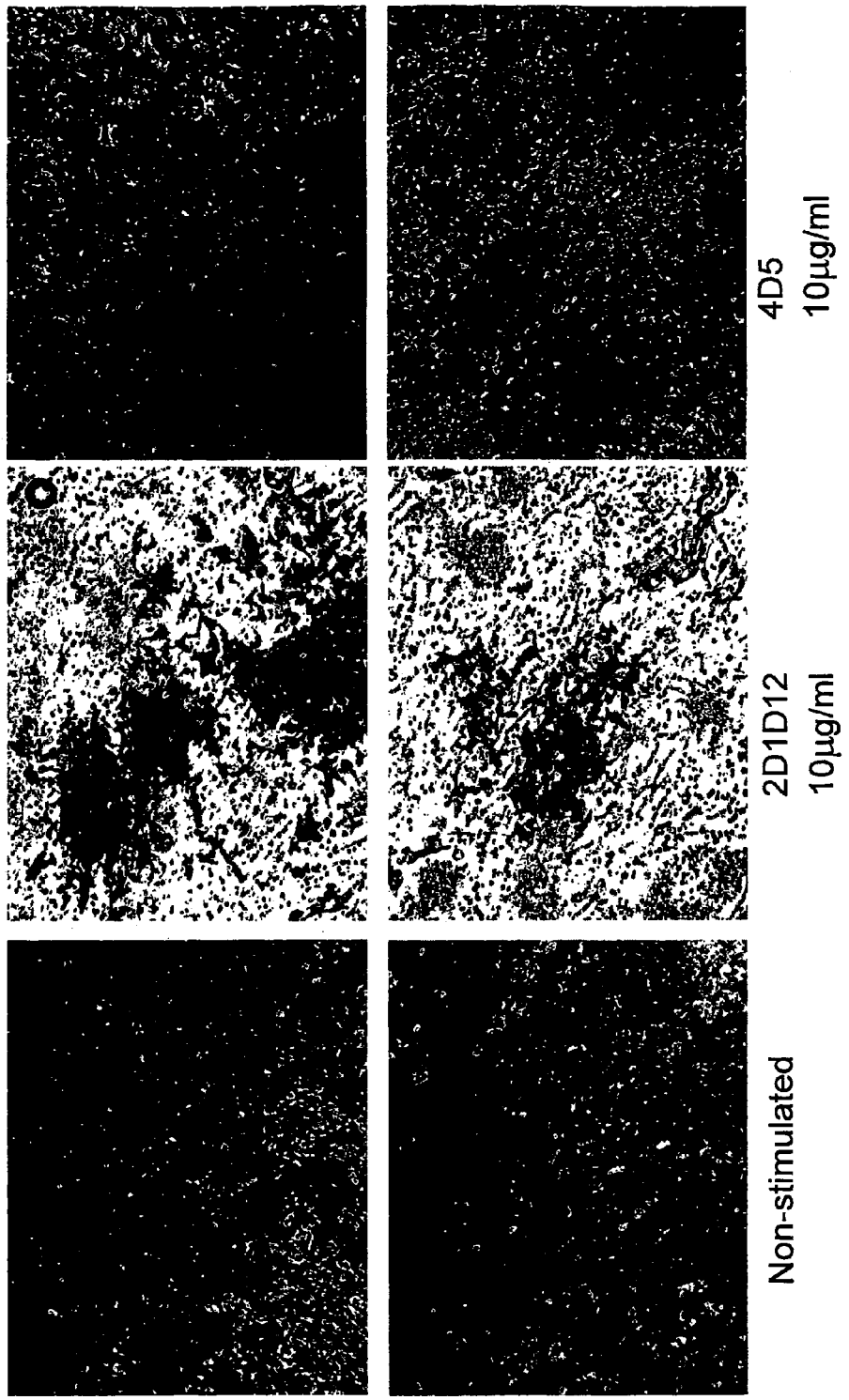

Monoclonal Antibodies 1B4C3 and 2D1D12 Inhibit Proliferation and Migration of Breast Cancer Cell Lines MDA-MB-435S and Melanoma Cell Line Mel-Juso To evaluate the inhibitory function of 1B4C3 and 2D1D12 on cell cycle progression and tumor invasion, we performed BrdU-Incorporation and invasion assays (FIG. 11).

We saw a robust decrease in β-HRG stimulated BrdU-incorporation in MDA-MB-435S and Mel-Juso cells pretreated with 2D1D12 (FIG. 11A). Invasion assays revealed that anti-HER3 antibodies 2D1D12 and 1B4C3 substantially decreased invasiveness of MDA-MB-435S breast cancer and Mel-Juso melanoma cells. Surprisingly HER2 antibody 4D5 only showed an inhibition in MDA-MB-435S but not in the melanoma cell line Mel-Juso although the receptor is expressed at the cell surface (FIG. 11B, C and FIG. 8A, B). Our results suggest the use of anti-HER3 antibodies for the treatment of breast cancer and melanoma.

Monoclonal Antibody 2D1d 12 Inhibits Heregulin-Stimulated Phosphorylation of PYK2

Figure 12:
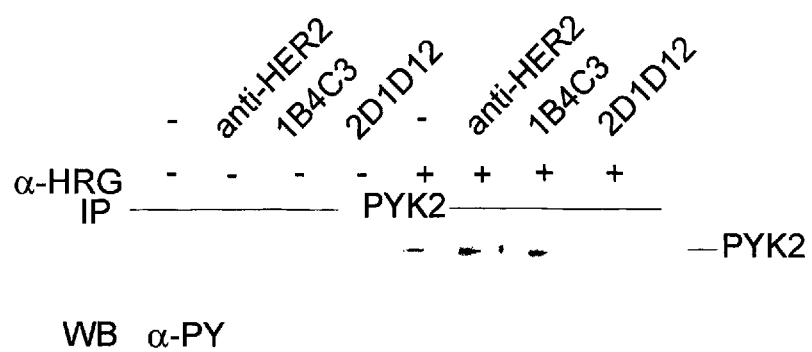
FIG. 12A shows quiescent SF767 human glioma cells pretreated with anti-HER2, 1B4C3 or 2D1D12 and stimulated or unstimulated with α-HRG, immunoprecipitated with PYK2 and blotted against phosphotyrosine (PY).
FIG. 12B shows Western blots of whole cell lysates of quiescent SF767 human glioma cells pretreated with anti-HER2, 1B4C3 or 2D1D12 and stimulated or unstimulated with α-HRG, blotted with α-phospho-ERK and reprobed with α-ERK.
Figure 12:
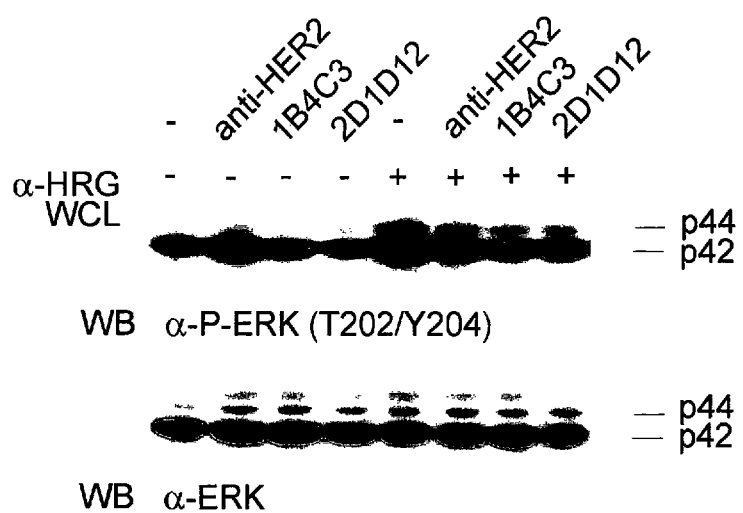

We previously demonstrated that the intracellular tyrosine kinase PYK2 associates with and is phosphorylated by HER3, suggesting that PYK2 functions as a mediator of HER3 activities. Consistent with this, dominant-negative PYK2 inhibited HRG-mediated invasion of glioma cells. Therefore, we wanted to explore the effect of anti-HER3 antibodies on HRG-induced PYK2 tyrosine phosphorylation. We pretreated quiescent SF767 human glioma cells with anti-HER2, 1B4C3 and 2D1D12 and subsequently stimulated the cells with α-HRG. After lysis and normalising for equal protein amounts, we immunoprecipitated PYK2 and blotted against phosphotyrosine (PY). We observed that whereas anti-HER2 and 1B4C3 had no inhibitory effect on tyrosine phosphorylation of PYK2, 2D1D12 markedly decreased PYK2 tyrosine phosphorylation (FIG. 12A). Thus, anti-HER3 antibodies are effective in inhibiting HRG-induced tyrosine phosphorylation of PYK2.

By probing immunoblots of WCL with phospho-ERK antibodies we observed that pretreating the cells with anti-HER2, 1B4C3 and 2D1D12 inhibited α-HRG activated ERK2 phosphorylation (FIG. 12B middle panel). Reprobing with ERK antibodies confirmed equal amount of loaded protein (FIG. 12B lower panel). Again, our data show that HER3 antibodies downregulate HRG-mediated signaling events in MDA-MB-435S, Mel-Juso and SF767. Furthermore, our analysis suggests that antibodies directed against ectodomains of HER2 and HER3 modulate differential signaling, leading to distinct responses of downstream effector proteins.

The invention claimed is:

1. A pharmaceutical composition comprising an inhibitor of HER3 activity and a pharmaceutically acceptable carrier or diluent, wherein binding of said inhibitor to HER3 reduces HER3 mediated signal transduction, wherein the inhibitor is antibody 1B4C3 produced by hybridoma cell line DSM ACC 2527, fragments thereof or recombinant derivatives thereof, wherein said fragments or recombinant derivatives comprises all six CDRs of said antibody 1B4C3.

2. The composition of claim 1 comprising a further active agent.

3. The composition of claim 1 for diagnostic applications.

4. The composition of claim 1 for therapeutic applications.

5. The pharmaceutical composition of claim 1, wherein said antibody is antibody 1B4C3 produced by hybridoma cell line DSM ACC 2527.

6. The composition of claim 2, wherein the further active agent is tyrosine kinase inhibitor or a cytotoxic agent.

7. The composition of claim 1, wherein said antibody or said antibody fragment thereof binds glycosylated forms of HER3 in the presence of deglycosylated forms of HER3 with an affinity that is detectable by western blot analysis.

8. A hybridoma cell line DSM ACC 2527 or a cell line derived therefrom, wherein said cell line derived therefrom produces 1B4C3.

9. A monoclonal antibody 1B4C3.

10. The monoclonal antibody 1B4C3 of claim 9, wherein said antibody is produced by hybridoma cell line DSM ACC 2527.

11. A monoclonal antibody 2D1D12 which is produced by hybridoma cell line DSM ACC 2517.

* * * * *